US009175245B2

(12) United States Patent
Allen et al.

(10) Patent No.: US 9,175,245 B2
(45) Date of Patent: Nov. 3, 2015

(54) FATTY AMIDES AND DERIVATIVES FROM NATURAL OIL METATHESIS

(75) Inventors: Dave R. Allen, Chicago, IL (US);
Marcos Alonso, Chicago, IL (US);
Randal J. Bernhardt, Antioch, IL (US);
Aaron Brown, Chicago, IL (US); Kelly Buchek, Hoffman Estates, IL (US);
Sangeeta Ganguly-Mink, Chicago, IL (US); Brian Holland, Deerfield, IL (US); Gary Luebke, Chicago, IL (US);
Renee Luka, Park Ridge, IL (US);
Andrew D. Malec, Chicago, IL (US);
Ronald A. Masters, Glenview, IL (US);
Dennis S. Murphy, Libertyville, IL (US); Irene Shapiro, Buffalo Grove, IL (US); Patti Skelton, Winder, GA (US);
Brian Sook, Lawrenceville, GA (US);
Michael R. Terry, Gurnee, IL (US);
Gregory Wallace, Chicago, IL (US);
Laura Lee Whitlock, Highland Park, IL (US); Michael Wiester, Chicago, IL (US); Patrick Shane Wolfe, Palatine, IL (US); Lena Titievsky, Chicago, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 13/878,556

(22) PCT Filed: Oct. 25, 2011

(86) PCT No.: PCT/US2011/057597
§ 371 (c)(1),
(2), (4) Date: May 15, 2013

(87) PCT Pub. No.: WO2012/061094
PCT Pub. Date: May 10, 2012

(65) Prior Publication Data
US 2013/0225470 A1     Aug. 29, 2013

Related U.S. Application Data

(60) Provisional application No. 61/406,570, filed on Oct. 25, 2010, provisional application No. 61/406,556, filed on Oct. 25, 2010, provisional application No. 61/406,547, filed on Oct. 25, 2010.

(51) Int. Cl.
*C11D 3/32*     (2006.01)
*C11C 3/08*     (2006.01)
(Continued)

(52) U.S. Cl.
CPC . *C11C 3/08* (2013.01); *A01N 25/02* (2013.01); *A01N 25/04* (2013.01); *A01N 25/30* (2013.01); *A01N 33/12* (2013.01); *A01N 37/18* (2013.01); *A01N 37/44* (2013.01); *A01N 41/04* (2013.01); *A61K 8/416* (2013.01); *A61K 8/42* (2013.01); *A61K 8/44* (2013.01); *A61K 8/466* (2013.01); *A61K 8/92* (2013.01); *A61Q 5/12* (2013.01); *A61Q 19/10* (2013.01); *A62D 1/0071* (2013.01); *B01F 17/0028* (2013.01); *B01F 17/0057* (2013.01); *C07C 69/533* (2013.01); *C07C 69/593* (2013.01); *C07C 209/12* (2013.01); *C07C 211/21* (2013.01); *C07C 219/08* (2013.01); *C07C 231/12* (2013.01); *C07C 237/16* (2013.01); *C07C 303/18* (2013.01); *C08G 65/2615* (2013.01); *C08K 5/01* (2013.01);
(Continued)

(58) Field of Classification Search
CPC ........................................................ C11D 3/32
USPC .......................................................... 510/501
See application file for complete search history.

(56) References Cited

U.S. PATENT DOCUMENTS 2,653,970 A   9/1953   Fessler et al.
3,169,142 A   2/1965   Knaggs et al.
(Continued)

FOREIGN PATENT DOCUMENTS

WO   WO-2008048522   4/2008
WO   WO-2011080208   11/2011
(Continued)

OTHER PUBLICATIONS

Schmitz et al. "Cleavage of spirooxaziridines by the action of ferrous sulfate" Bull. Acad. Sci. USSR, Div. Chem. Sci. (Engl. Transl.), vol. 40, No. 4 (Apr. 1, 1991) pp. 849-853.
(Continued)

*Primary Examiner* — Charles Boyer
(74) *Attorney, Agent, or Firm* — Dilworth IP LLC

(57) ABSTRACT

Fatty amide compositions and their derivatives are disclosed. The fatty amides comprise a reaction product of a metathesis-derived $C_{10}$-$C_{17}$ monounsaturated acid, octadecene-1,18-dioic acid, or their ester derivatives with a primary or secondary amine. Derivatives made by reducing, quaternizing, sulfonating, alkoxylating, sulfating, and sulfitating the fatty amide are also included. The amine reactant can be diethylenetriamine or (2-aminoethyl)ethanolamine, which provide imidazoline amides or esters, respectively. In one aspect, the ester derivative of the $C_{10}$-$C_{17}$ monounsaturated acid or octadecene-1,18-dioic acid is a lower alkyl ester. In other aspects, the ester derivative is a modified triglyceride made by self-metathesis of a natural oil or an unsaturated triglyceride made by cross-metathesis of a natural oil with an olefin. The compositions are valuable for cleaners, fabric treatment, hair conditioning, personal care, antimicrobial compositions, agricultural uses, and oil field applications.

12 Claims, No Drawings

(51) Int. Cl.

| | | |
|---|---|---|
| C07C 69/533 | (2006.01) | |
| C07C 69/593 | (2006.01) | |
| C11D 1/28 | (2006.01) | |
| C11D 1/74 | (2006.01) | |
| B01F 17/00 | (2006.01) | |
| C11D 1/83 | (2006.01) | |
| C11D 1/94 | (2006.01) | |
| C07C 211/21 | (2006.01) | |
| C07C 237/16 | (2006.01) | |
| A01N 25/04 | (2006.01) | |
| A01N 33/12 | (2006.01) | |
| A01N 37/18 | (2006.01) | |
| A01N 37/44 | (2006.01) | |
| A01N 41/04 | (2006.01) | |
| A61K 8/41 | (2006.01) | |
| A61K 8/42 | (2006.01) | |
| A61K 8/44 | (2006.01) | |
| A61K 8/46 | (2006.01) | |
| A61Q 5/12 | (2006.01) | |
| A61Q 19/10 | (2006.01) | |
| A62D 1/02 | (2006.01) | |
| C09K 8/00 | (2006.01) | |
| C09K 15/28 | (2006.01) | |
| C11D 1/62 | (2006.01) | |
| C11D 1/90 | (2006.01) | |
| C11D 1/92 | (2006.01) | |
| C11D 1/04 | (2006.01) | |
| A01N 25/02 | (2006.01) | |
| A61K 8/92 | (2006.01) | |
| C08K 5/01 | (2006.01) | |
| C08K 5/20 | (2006.01) | |
| C11C 3/00 | (2006.01) | |
| C11D 3/48 | (2006.01) | |
| C07C 219/08 | (2006.01) | |
| A01N 25/30 | (2006.01) | |
| C07C 209/12 | (2006.01) | |
| C07C 231/12 | (2006.01) | |
| C07C 303/18 | (2006.01) | |
| C11D 1/00 | (2006.01) | |
| C11D 1/65 | (2006.01) | |
| C08G 65/26 | (2006.01) | |

(52) U.S. Cl.
CPC ... *C08K 5/20* (2013.01); *C09K 8/00* (2013.01); *C09K 15/28* (2013.01); *C11C 3/00* (2013.01); *C11D 1/002* (2013.01); *C11D 1/04* (2013.01); *C11D 1/28* (2013.01); *C11D 1/62* (2013.01); *C11D 1/652* (2013.01); *C11D 1/74* (2013.01); *C11D 1/83* (2013.01); *C11D 1/90* (2013.01); *C11D 1/92* (2013.01); *C11D 1/94* (2013.01); *C11D 3/48* (2013.01)

(56) References Cited

U.S. PATENT DOCUMENTS

| | | | |
|---|---|---|---|
| 3,258,474 | A | 6/1966 | Rose et al. |
| 3,544,613 | A | 12/1970 | Knaggs et al. |
| 3,642,977 | A | 2/1972 | Hewitt et al. |
| 3,696,043 | A | 10/1972 | Labarge et al. |
| 3,759,847 | A | 9/1973 | Martineau et al. |
| 4,087,457 | A | 5/1978 | Convers et al. |
| 4,148,821 | A | 4/1979 | Nussbaum et al. |
| 4,275,013 | A | 6/1981 | Tokosh et al. |
| 4,545,941 | A | 10/1985 | Rosenburg |
| 4,668,422 | A | 5/1987 | Malik et al. |
| 4,948,531 | A * | 8/1990 | Fuggini et al. ............ 510/400 |
| 4,956,107 | A | 9/1990 | Guterriez et al. |
| 5,108,661 | A * | 4/1992 | Boiteux et al. ............ 516/15 |
| 5,388,644 | A | 2/1995 | Romocki |
| 5,482,908 | A | 1/1996 | Le-khac |
| 5,622,911 | A | 4/1997 | Hasebe et al. |
| 5,750,492 | A | 5/1998 | Contet et al. |
| 5,783,534 | A | 7/1998 | Wahle et al. |
| 5,939,059 | A | 8/1999 | Franklin et al. |
| 6,004,913 | A | 12/1999 | Iacobucci et al. |
| 6,057,283 | A | 5/2000 | aus des Kahmen et al. |
| 6,107,498 | A | 8/2000 | Maisonneuve et al. |
| 6,306,805 | B1 | 10/2001 | Bratescu et al. |
| 7,214,650 | B2 | 5/2007 | Kasturi et al. |
| 7,304,026 | B2 | 12/2007 | Heibel et al. |
| 7,393,907 | B2 | 7/2008 | Imuta et al. |
| 7,576,227 | B2 | 8/2009 | Bicerano et al. |
| 7,714,087 | B2 | 5/2010 | Imuta et al. |
| 7,960,599 | B2 | 6/2011 | Millis et al. |
| 8,067,610 | B2 | 11/2011 | Schrodi |
| 2001/0044405 | A1 * | 11/2001 | Perella et al. ............ 510/433 |
| 2005/0274399 | A1 | 12/2005 | Heise et al. |
| 2006/0128601 | A1 | 6/2006 | Pereira et al. |
| 2006/0180677 | A1 | 8/2006 | McManic et al. |
| 2007/0010680 | A1 | 1/2007 | Yajima et al. |
| 2007/0054835 | A1 | 3/2007 | Corona, III et al. |
| 2007/0202188 | A1 | 8/2007 | Ley |
| 2008/0033026 | A1 | 2/2008 | Zullo et al. |
| 2009/0143527 | A1 | 6/2009 | Thames et al. |
| 2009/0181850 | A1 | 7/2009 | Stern et al. |
| 2009/0264672 | A1 * | 10/2009 | Abraham et al. ............ 560/190 |
| 2010/0145086 | A1 | 6/2010 | Schrodi et al. |
| 2010/0282467 | A1 | 11/2010 | Hutchison et al. |
| 2011/0113679 | A1 | 5/2011 | Cohen et al. |
| 2011/0124505 | A1 | 5/2011 | Merlet et al. |
| 2011/0313180 | A1 | 12/2011 | Uptain et al. |
| 2012/0010303 | A1 | 1/2012 | Mujkic et al. |
| 2012/0071676 | A1 | 3/2012 | Schrodi et al. |
| 2012/0197031 | A1 | 8/2012 | Firth et al. |
| 2013/0035502 | A1 | 2/2013 | Cohen et al. |
| 2013/0035532 | A1 | 2/2013 | Schrodi |

FOREIGN PATENT DOCUMENTS

| | | | |
|---|---|---|---|
| WO | WO-2012006324 | | 1/2012 |
| WO | 2012006324 | * | 12/2012 |

OTHER PUBLICATIONS

Concellon et al., "Steriospecific Cyclopropanation of Highly Substituted C-C Double Bonds Promoted by CrCl 2. Stereoselective Synthesis of Cyclopropanecarboxamides and Cyclopropyl Ketones" Org. Lett., vol. 9, No. 16 (Aug. 1, 2007) pp. 2981-2984.

Tits et al. "Ozonisation des amides ethyleniques", Bull. Soc. Chim. Belg., vo. 57, No. 1-3 (Jan. 1, 1948). pp. 50-64.

Taylor et al. , J. Am Chem. Soc., vol. 72, No. 9, (Sep. 19, 1950) pp. 4263-4265.

Extended European Search Report mailed in EP Application No. 11838499.99 on Aug. 21, 2013.

Tetrahedron 68 2012 , 1117.

Appl. Catal.A. 346 2009, 158.

J.C. Mol., Topics in Catalysis 27 2004, 97.

J. C. Mol., Green Chem., 4 2002, 5.

* cited by examiner

FATTY AMIDES AND DERIVATIVES FROM NATURAL OIL METATHESIS

FIELD OF THE INVENTION

The invention relates to fatty amides and derivative compositions that originate from renewable resources, particularly natural oils and their metathesis products.

BACKGROUND OF THE INVENTION

Fatty amides are reaction products of fatty acids or esters (including oils and glycerides) and an amine. The amine may be ammonia or a primary or secondary amine (e.g., dimethylamine, ethanolamine, isopropanolamine, or diethanolamine). Another important class of fatty amide product are imidazolines produced by reacting a fatty acid or ester with diethylenetriamine (DETA), (2-aminoethyl)ethanolamine (AEEA), or the like. The imidazolines are particularly interesting because they can be quaternized to enhance water solubility and extend their applicability. Fatty amides, including imidazolines and their quats, have utility in a wide range of end-use applications, including fabric softening (see U.S. Pat. No. 7,304,026 and U.S. Pat. Appl. Publ. No. 2007/0054835), hair care (U.S. Pat. Nos. 3,642,977 and 6,306,805, and U.S. Pat. Appl. Publ. No. 2006/0128601), detergents (U.S. Pat. Nos. 3,696,043; 3,759,847; and 6,057,283), hand-soaps (U.S. Pat. No. 4,668,422), agricultural adjuvants (U.S. Pat. No. 5,622,911 and U.S. Pat. Appl. Publ. No. 2011/0124505), and functionalized monomers (U.S. Pat. Appl. No. 2009/0143527).

The fatty acids or esters used to make fatty amides are usually made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. The unsaturation in these acids has either exclusively or predominantly cis-configuration.

Recent improvements in metathesis catalysts (see J. C. Mol, *Green Chem.* 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, fatty amides and their derivatives made from these feedstocks appear to be unknown. Moreover, fatty amides and their derivatives have not been made from the $C_{18}$ unsaturated diesters that can be made readily by self-metathesis of a natural oil.

In sum, traditional sources of fatty acids and esters used for making fatty amides and their derivatives generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants). New $C_{18}$ difunctional fatty amides and derivatives are also potentially available from oil or $C_{10}$ unsaturated acid or ester self-metathesis. In addition to an expanded variety of precursors, the unsaturation present in the precursors allows for further functionalization, e.g., by sulfonation or sulfitation.

SUMMARY OF THE INVENTION

In one aspect, the invention relates to fatty amide compositions. The amides comprise a reaction product of a metathesis-derived $C_{10}$-$C_{17}$ monounsaturated acid, octadecene-1,18-dioic acid, or their ester derivatives with ammonia or a primary or secondary amine. The invention includes derivatives made by one or more of reducing, quaternizing, sulfonating, alkoxylating, sulfating, and sulfitating the fatty amide. In particular aspects, the amine reactant is diethylenetriamine or (2-aminoethyl)-ethanolamine, which provide imidazoline amides or esters, respectively. In one aspect, the ester derivative of the $C_{10}$-$C_{17}$ monounsaturated acid or octadecene-1,18-dioic acid is a lower alkyl ester. In other aspects, the ester derivative is a modified triglyceride made by self-metathesis of a natural oil or an unsaturated triglyceride made by cross-metathesis of a natural oil with an olefin. Fatty amides and their derivatives are valuable for a wide variety of end uses, including cleaners, fabric treatment, hair conditioning, personal care (liquid cleansing products, conditioning bars, oral care products), antimicrobial compositions, agricultural uses, and oil field applications.

DETAILED DESCRIPTION OF THE INVENTION

In one aspect, the invention relates to fatty amide compositions that comprise reaction products of a metathesis-derived $C_{10}$-$C_{17}$ monounsaturated acid, octadecene-1,18-dioic acid, or their ester derivatives with ammonia or a primary or secondary amine.

The $C_{10}$-$C_{17}$ monounsaturated acid, octadecene-1,18-dioic acid, or their ester derivatives used as a reactant is derived from metathesis of a natural oil. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like. Self-metathesis of the natural oil or a $C_{10}$ acid or ester precursor (e.g., methyl 9-decenoate) provides the $C_{18}$ diacid or diester in optimal yield when it is the desired product.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis-isomers.

Although a high proportion of trans-geometry (particularly trans-$\Delta^9$ geometry) may be desirable in the metathesis-derived fatty amides and derivatives of the invention, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal. A: General* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts different physical properties to fatty amide compositions made from them, including, for example, modified physical form, melting range, compactability, and other important properties. These differences should allow formulators that use fatty amides greater latitude or expanded choice as they use the fatty amides or derivatives in cleaners, fabric treatment, personal care, agricultural uses, and other end uses.

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, typically by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{19}$ alkyl esters, which are essentially spectators in the metathesis reaction. The rest of the product mixture depends on whether cross- or self-metathesis is used. When the natural oil is self-metathesized and then transesterified, the alkyl ester mixture will include a $C_{18}$ unsaturated diester. When the natural oil is cross-metathesized with an α-olefin and the product mixture is transesterified, the resulting alkyl ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. As is demonstrated in the examples below, the $C_{10}$ unsaturated alkyl ester is readily separated from the $C_{11}$ to $C_{17}$ unsaturated alkyl ester and each is easily purified by fractional distillation. These alkyl esters are excellent starting materials for making the inventive fatty amide compositions.

Natural oils suitable for use as a feedstock to generate the $C_{10}$-$C_{17}$ monounsaturated acid, octadecene-1,18-dioic acid, or their ester derivatives from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to inventive fatty amide compositions.

An alternative to using a natural oil as a feedstock to generate the $C_{10}$-$C_{17}$ monounsaturated acid, octadecene-1,18-dioic acid, or their ester derivatives from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb), or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first- and second-generation Grubbs catalysts, Grubbs-Hoveyda catalysts, and the like. Suitable alkylidene catalysts have the general structure:

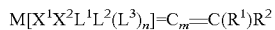

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β- or γ-with respect to the carbene carbon to provide the bidentate ligand. Examples of suitable Grubbs-Hoveyda catalysts appear in the '086 publication.

The structures below provide just a few illustrations of suitable catalysts that may be used:

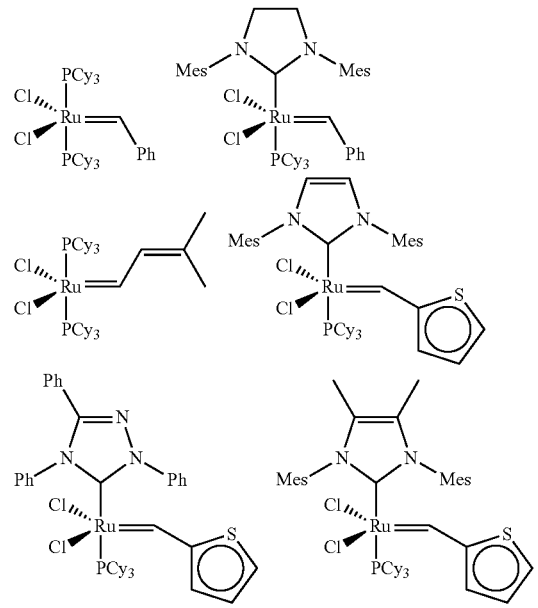

Heterogeneous catalysts suitable for use in the self- or cross-metathesis reaction include certain rhenium and molybdenum compounds as described, e.g., by J. C. Mol in Green Chem. 4 (2002) 5 at pp. 11-12. Particular examples are catalyst systems that include $Re_2C_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

The fatty amides are made by reacting a metathesis-derived $C_{10}$-$C_{17}$ monounsaturated acid, octadecene-1,18-dioic acid, or their ester derivatives with ammonia or a primary or secondary amine.

In one aspect, the ester derivative is a lower alkyl ester, especially a methyl ester. The lower alkyl esters are preferably generated by transesterifying a metathesis-derived triglyceride. For example, cross-metathesis of a natural oil with an olefin, followed by removal of unsaturated hydrocarbon metathesis products by stripping, and then transesterification of the modified oil component with a lower alkanol under basic conditions provides a mixture of unsaturated lower alkyl esters. The unsaturated lower alkyl ester mixture can be used "as is" to make inventive fatty amide mixtures or it can be purified to isolate particular alkyl esters prior to making fatty amides.

In another aspect, the ester derivative to be reacted with the ammonia or primary or secondary amine is the metathesis-derived triglyceride discussed in the preceding paragraph. Instead of transesterifying the metathesis-derived triglyceride with a lower alkanol to generate lower alkyl esters as described above, the metathesis-derived triglyceride, following olefin stripping, is reacted directly with ammonia or a primary or secondary amine to make an inventive fatty amide mixture.

The skilled person will appreciate that "ester derivative" here encompasses other acyl equivalents, such as acid chlorides, acid anhydrides, or the like, in addition to the lower alkyl esters and glyceryl esters discussed above.

Suitable primary or secondary amines have one or two hydrogens attached to the amino group. The remaining groups are typically alkyl or substituted alkyl groups, preferably $C_1$-$C_{10}$ alkyl, more preferably $C_1$-$C_4$ alkyl. Thus, suitable primary or secondary amines include ethylamine, isopropylamine, N,N-dimethylamine, N,N-diethylamine, N,N-diisopropylamine, and the like. In one preferred class of primary and secondary amines, a N or O atom is bonded to a carbon that is beta or gamma to the N atom of the amine. In some preferred primary or secondary amines, the nitrogen is attached to one $C_1$-$C_{10}$ alkyl group, preferably a $C_1$-$C_4$ alkyl group, and one hydroxyalkyl group having from 2 to 4 carbons. In other preferred primary or secondary amines, the nitrogen is attached to a hydrogen and two hydroxyalkyl groups having from 2 to 4 carbons each. Alkanolamines, which have an oxygen atom beta to the amine nitrogen, are particularly preferred. Suitable alkanolamines are well known and commercially available from BASF, Dow Chemical and other suppliers. They include, for example, ethanolamine, propanolamine, isopropanolamine, diethanolamine, N-methylethanolamine, N-methylisopropanolamine, N-ethylethanolamine, and the like, and mixtures thereof. Particularly preferred alkanolamines are ethanolamine, diethanolamine, and N-methylethanolamine, which are economical and readily available.

Suitable primary and secondary amines include alkoxylated derivatives of the compounds described above. Thus, for example, the amine used to make the fatty amide can be an amine-terminated polyether comprising 0.1 to 20 moles of ethylene oxide or propylene oxide per mole of —OH group in the alkanolamine.

The primary or secondary amine is advantageously diethylene triamine (DETA), (2-aminoethyl)ethanolamine (AEEA), or an alkoxylated derivative thereof. DETA and AEEA can react with two equivalents of a $C_{10}$-$C_{17}$ monounsaturated acid, octadecene-1,18-dioic acid, or their ester derivatives to give an imidazoline amide or ester, respectively, which have a tertiary nitrogen available for quaternization.

The fatty amides are made using a well-known process that provides a unique product mixture because of the unconventional starting mixture of acid or ester derivatives (including lower alkyl esters or triglycerides). The reactants are typically heated under conditions effective to convert the starting acid or ester to an amide. No catalyst is required, but a basic catalyst such as an alkoxide is optionally included. The reaction temperature is typically within the range of 40° C. to 300° C., preferably from 50° C. to 250° C., and more preferably from 50° C. to 200° C. The reaction mixture is heated until the starting ester, acid, or triglyceride is substantially consumed. The amide product can be purified by distillation, water washing, or other normal means if desired. Alternatively, the product is used "as is" and converted to other derivatives.

When imidazolines are the target, the reaction temperatures tend to be higher, a two-stage process is used, and an acid catalyst is used to promote cyclization. The starting ester is commonly heated with a tertiary amine catalyst (e.g., DABCO, 1,4-diazabicyclo[2.2.2]octane), and DETA or AEEA at 80° C. to 250° C. Additional DETA or AEEA is added to the reactor as needed. When the initial reaction is complete (as is usually indicated by no further distillate of an alcohol), an acid catalyst such as p-toluenesulfonic acid is added, and the mixture is heated at elevated temperature (e.g., 150° C. to 300° C., preferably from 180° C. to 250° C.) to effect the desired ring closure. Exemplary procedures are provided below.

The relative amounts of primary or secondary amine and ester or acid reactants used depend on the desired stoichiometry and is left to the skilled person's discretion. When the primary or secondary amine is ethanolamine, diethanolamine, isopropanolamine, or the like, it is preferred to use one mole of $C_{10}$ or $C_{12}$ acid or ester derivative per mole of amine. With DETA or AEEA, it is preferred to use two moles of $C_{10}$ to $C_{17}$ acid or ester derivative per mole of DETA or AEEA to enable production of an imidazoline. The examples below illustrate the variety of possible fatty amides available from a $C_{18}$ diacid or diester. In general, the molar ratio of amino groups in the primary or secondary amine to the acid or ester groups available is within the range of 0.1:1 to 3:1, preferably from 0.5:1 to 3:1, and more preferably from 1:1 to 3:1.

Some amides have the formula:

$$R^1CO-NR^2R^3$$

where $R^1$ is $R^4$—$C_9H_{16}$— or $R^5O_2C$—$C_{16}H_{30}$—; $R^4$ is hydrogen or $C_1$-$C_7$ alkyl; $R^5$ is substituted or unsubstituted alkyl, aryl, alkenyl, oxyalkylene, polyoxyalkylene, glyceryl ester, or a mono- or divalent cation; and each of $R^2$ and $R^3$ is independently H, $C_1$-$C_6$ alkyl, or —$CH_2CH_2OR^6$ where $R^6$ is H or $C_1$-$C_6$ alkyl. Preferably, $R^1$ is $R^4CH\!\!=\!\!CH$—$(CH_2)_7$— or $R^5O_2C$—$(CH_2)_7$—$CH\!\!=\!\!CH$—$(CH_2)_7$—.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, reaction products from modified triglycerides are complex mixtures. As another example, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

Some specific examples of $C_{10}$, $C_{12}$, $C_{14}$, and $C_{16}$-based fatty amides appear below:

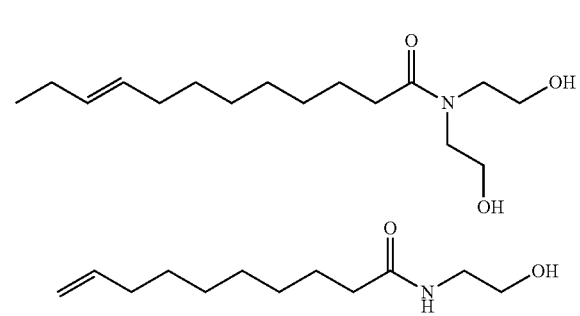

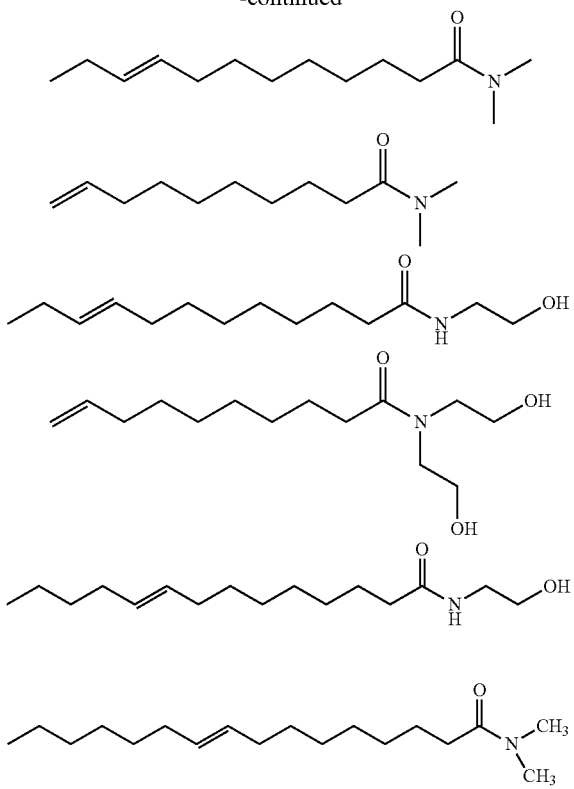

Some specific examples of $C_{10}$, $C_{12}$, $C_{14}$, and $C_{16}$-based imidazolines:

The fatty amide product mixture can be complex when the ester derivative reacted with the primary or secondary amine is a modified triglyceride made by self-metathesis of a natural oil and separation to remove olefins (see, e.g., the MTG and PMTG products described below) or an unsaturated triglyceride made by cross-metathesis of a natural oil and an olefin and separation to remove olefins (see, e.g., the UTG and PUTG products described below). As is evident from the reaction schemes, the MTG and PMTG products include an unsaturated $C_{18}$ diamide as a principal component, while the UTG and PUTG products include a $C_{10}$ unsaturated amide component and one or more $C_{11}$ to $C_{17}$ unsaturated amide components. (For example, with 1-butene as the cross-metathesis reactant, as illustrated, a $C_{12}$ unsaturated amide component results). Other components of the product mixtures are glycerin and saturated or unsaturated fatty amides derived from the primary or secondary amine. Despite the complexity, purification to isolate a particular species is often neither economical nor desirable for good performance.

Thus, in one aspect, the fatty amide is produced by reacting ammonia or a primary or secondary amine with a modified triglyceride made by self-metathesis of a natural oil. Self-metathesis of the natural oil provides a mixture of olefins and a modified triglyceride that is enriched in a $C_{18}$ unsaturated diester component along with $C_{16}$-$C_{18}$ saturated diesters. The olefins are stripped out, usually with heat and reduced pressure. When the self-metathesis product is reacted directly with the ammonia or primary or secondary amine, a complex mixture results in which amino groups of the ammonia or primary or secondary amine completely or partially displace glycerin from the glyceryl esters to form amide functionalities. Representative fatty amide products below are made by reacting a primary or secondary amine with MTG-0 (modified triglyceride from soybean oil) or PMTG-0 (modified triglyceride from palm oil). One example is MTG-17, a reaction product of MTG-0 and ethanolamine:

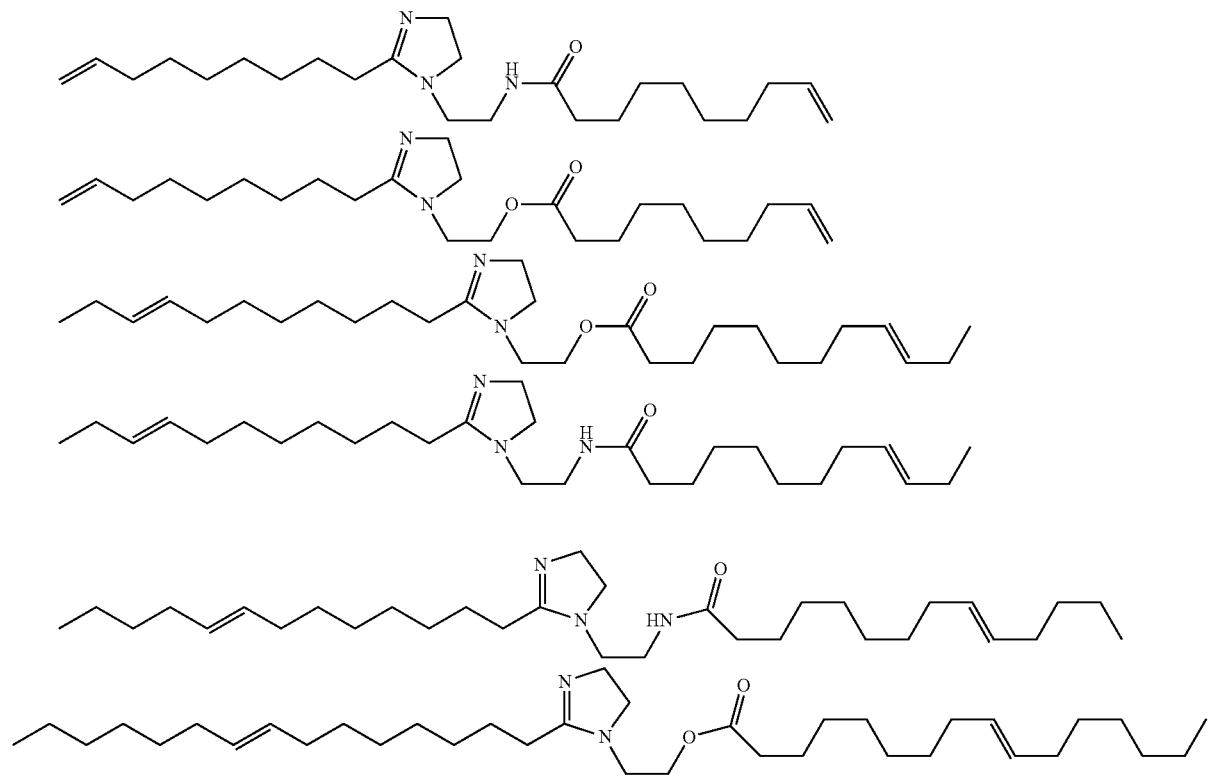

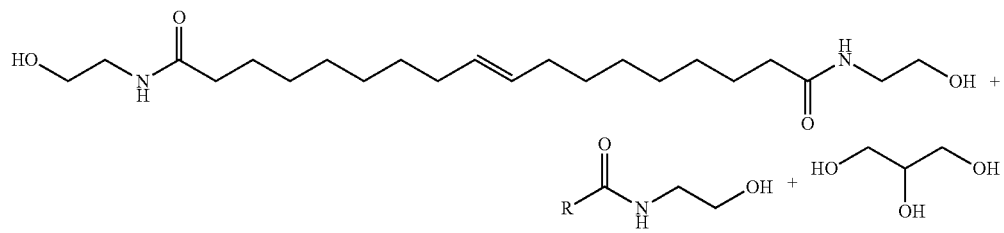

R = C16, C18 Sat. + Unsat.

In another aspect, the fatty amide is produced by reacting ammonia or a primary or secondary amine with an unsaturated triglyceride made by cross-metathesis of a natural oil with an olefin. Cross-metathesis of the natural oil and olefin provides a mixture of olefins and an unsaturated triglyceride that is rich in $C_{10}$ and $C_{12}$ unsaturated esters as well as $C_{16}$-$C_{18}$ saturated esters. The olefins are stripped out, usually with heat and reduced pressure. When the cross-metathesis product is reacted with the ammonia or primary or secondary amine, a complex mixture results in which amino groups of the ammonia or primary or secondary amine completely or partially displace glycerin from the glyceryl esters to form amide functionalities. Representative fatty amide products below are made by reacting a primary or secondary amine with UTG-0 (unsaturated triglyceride from cross-metathesis of soybean oil and 1-butene) or PUTG-0 (unsaturated triglyceride from cross-metathesis of palm oil with 1-butene). One example is the reaction of PUTG-0 with isopropanolamine to make the MIPA amide product, PUTG-17:

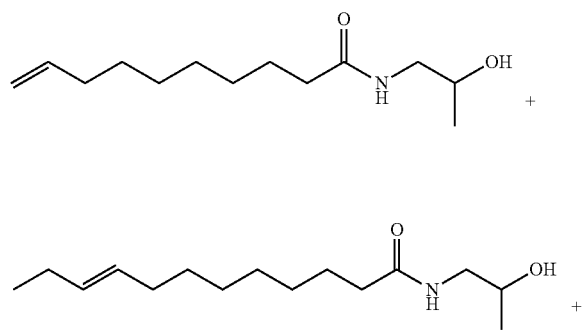

-continued

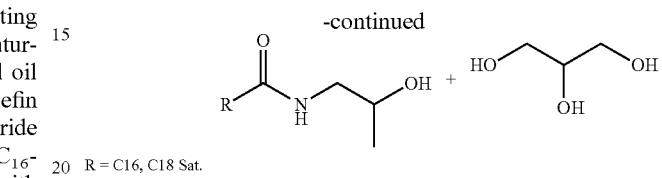

R = C16, C18 Sat.

The reaction to form the fatty amides from lower alkyl esters can be performed under a nitrogen sparge or under vacuum to remove liberated alcohol. When glyceride esters are reactants, the liberated glycerin need not be removed from the product. The reaction is considered complete when the residual glyceride content of the product reaches the desired level.

The invention includes derivatives made by one or more of reducing, quaternizing, sulfonating, alkoxylating, sulfating, and sulfitating the fatty amide product. Methods for quaternizing tertiary amines are well known in the art. Quaternization of the imidazolines is accomplished by warming them with a quaternizing agent such as an alkyl halide or dialkyl sulfate. Specific examples include dimethylsulfate, methyl chloride, epichlorohydrin, benzyl chloride, alkali metal chloroacetates, and the like. Dimethyl sulfate is particularly preferred. The reaction is generally performed at a temperature within the range of 30° C. to 150° C., preferably from 65° C. to 100° C., or more preferably from 80° C. to 90° C. The amount of quaternizing agent used is typically 0.8 to 1.2 mole equivalents based on the tertiary nitrogen content. The reaction is deemed complete when the free amine value is in the desired range as determined by perchloric acid titration or other suitable analytical method. Suitable methods for quaternizing imidazolines are disclosed in U.S. Pat. Nos. 5,750,492; 5,783,534; 5,939,059; and 6,004,913, the teachings of which are incorporated herein by reference.

Examples of suitable $C_{10}$, $C_{12}$, $C_{14}$, and $C_{16}$-based quaternized imidazolines:

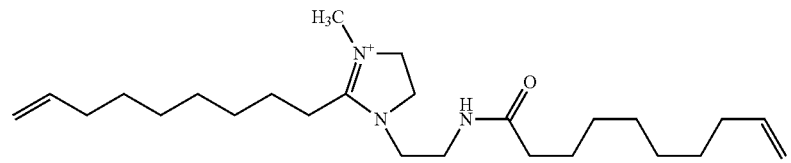

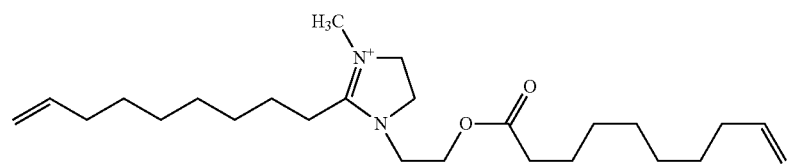

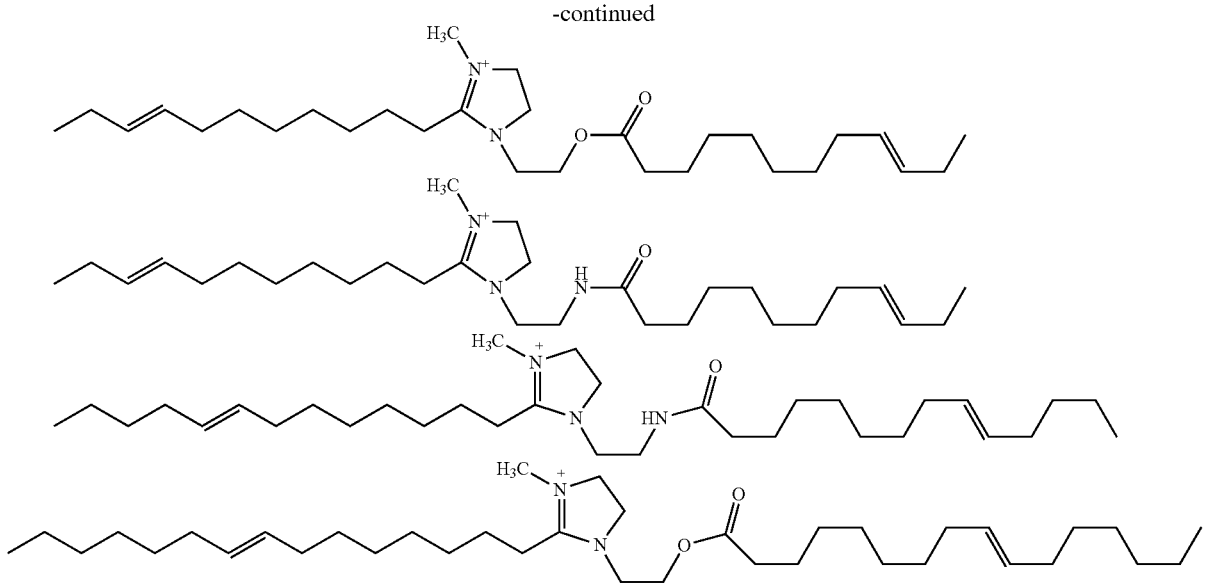

The fatty amides and quaternized fatty amides have unsaturation that can be sulfonated or sulfitated if desired. Sulfonation is performed using well-known methods, including reacting the olefin with sulfur trioxide. Sulfonation may optionally be conducted using an inert solvent. Non-limiting examples of suitable solvents include liquid $SO_2$, hydrocarbons, and halogenated hydrocarbons. In one commercial approach, a falling film reactor is used to continuously sulfonate the olefin using sulfur trioxide. Other sulfonating agents can be used with or without use of a solvent (e.g., chlorosulfonic acid, fuming sulfuric acid), but sulfur trioxide is generally the most economical. The sultones that are the immediate products of reacting olefins with $SO_3$, chlorosulfonic acid, and the like may be subsequently subjected to a hydrolysis reaction with aqueous caustic to afford mixtures of alkene sulfonates and hydroxyalkane sulfonates. Suitable methods for sulfonating olefins are described in U.S. Pat. Nos. 3,169,142; 4,148,821; and U.S. Pat. Appl. Publ. No. 2010/0282467, the teachings of which are incorporated herein by reference.

Sulfitation is accomplished by combining an olefin in water (and usually a cosolvent such as isopropanol) with at least a molar equivalent of a sulfitating agent using well-known methods. Suitable sulfitating agents include, for example, sodium sulfite, sodium bisulfite, sodium metabisulfite, or the like. Optionally, a catalyst or initiator is included, such as peroxides, iron, or other free-radical initiators. Typically, the reaction mixture is conducted at 15-100° C. until the reaction is reasonably complete. Suitable methods for sulfitating olefins appear in U.S. Pat. Nos. 2,653,970; 4,087,457; 4,275,013, the teachings of which are incorporated herein by reference.

When the fatty amide has hydroxyl functionality, it can also be alkoxylated, sulfated, or both using well-known techniques. For instance, a hydroxyl-terminated fatty amide can be alkoxylated by reacting it with ethylene oxide, propylene oxide, or a combination thereof to produce an alkoxylated alcohol. Alkoxylations are usually catalyzed by a base (e.g., KOH), but other catalysts such as double metal cyanide complexes (see U.S. Pat. No. 5,482,908) can also be used. The oxyalkylene units can be incorporated randomly or in blocks. The hydroxyl-functional fatty amide can be sulfated, with or without a prior alkoxylation, and neutralized to give an alcohol sulfate according to known methods (see, e.g., U.S. Pat. No. 3,544,613, the teachings of which are incorporated herein by reference).

The fatty amides and their reduced, quaternized, sulfonated, alkoxylated, sulfated, and sulfitated derivatives can be incorporated into many compositions for use as, for example, surfactants, emulsifiers, skin-feel agents, film formers, rheological modifiers, biocides, biocide potentiators, solvents, release agents, and conditioners. The compositions find value in diverse end uses, such as personal care (liquid cleansing products, conditioning bars, oral care products), household products (liquid and powdered laundry detergents, liquid and sheet fabric softeners, hard and soft surface cleaners, sanitizers and disinfectants), and industrial or institutional cleaners.

The fatty amides and derivatives can be used in emulsion polymerizations, including processes for the manufacture of latex. They can be used as surfactants, wetting agents, dispersants, or solvents in agricultural applications, as inert ingredients in pesticides, or as adjuvants for delivery of pesticides for crop protection, home and garden, and professional applications. The fatty amides and derivatives can also be used in oil field applications, including oil and gas transport, production, stimulation and drilling chemicals, reservoir conformance and enhancement uses, and specialty foamers. The compositions are also valuable as foam moderators or dispersants for the manufacture of gypsum, cement wall board, concrete additives and firefighting foams. The compositions are used as coalescents for paints and coatings, and as polyurethane-based adhesives.

In food and beverage processing, the fatty amides and derivatives can be used to lubricate the conveyor systems used to fill containers. When combined with hydrogen peroxide, the fatty amides and derivatives can function as low foaming disinfectants and sanitization agents, odor reducers, and as antimicrobial agents for cleaning and protecting food or beverage processing equipment. In industrial, institutional and laundry applications, the fatty amides and derivatives, or their combination with hydrogen peroxide, can be used to remove soil and sanitize and disinfect fabrics and as antimicrobial film-forming compositions on hard surfaces.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

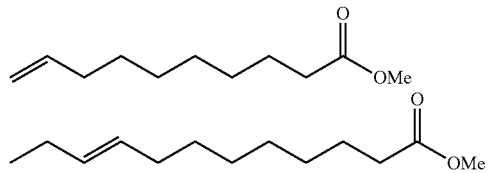

The procedures of U.S. Pat. Appl. Publ. No. 2011/0113679, the teachings of which are incorporated herein by reference, are used to generate feedstocks C10-0 and C12-0 as follows:

Example 1A

Cross-Metathesis of Soybean Oil and 1-Butene

A clean, dry, stainless-steel jacketed 5-gallon Parr reactor equipped with a dip tube, overhead stirrer, internal cooling/heating coils, temperature probe, sampling valve, and relief valve is purged with argon to 15 psig. Soybean oil (SBO, 2.5 kg, 2.9 mol, Costco, $M_n$=864.4 g/mol, 85 weight % unsaturation, sparged with argon in a 5-gal container for 1 h) is added to the Parr reactor. The reactor is sealed, and the SBO is purged with argon for 2 h while cooling to 10° C. After 2 h, the reactor is vented to 10 psig. The dip tube valve is connected to a 1-butene cylinder (Airgas, CP grade, 33 psig headspace pressure, >99 wt. %) and re-pressurized to 15 psig with 1-butene. The reactor is again vented to 10 psig to remove residual argon. The SBO is stirred at 350 rpm and 9-15° C. under 18-28 psig 1-butene until 3 mol 1-butene per SBO olefin bond are transferred into the reactor (~2.2 kg 1-butene over 4-5 h).

A toluene solution of [1,3-bis-(2,4,6-trimethylphenyl)-2-imidazolidinylidene]-dichlororuthenium(3-methyl-2-butenylidene)(tricyclohexylphosphine) (C827, Materia) is prepared in a Fischer-Porter pressure vessel by dissolving 130 mg catalyst in 30 g of toluene (10 mol ppm per mol olefin bond of SBO). The catalyst mixture is added to the reactor via the reactor dip tube by pressurizing the headspace inside the Fischer-Porter vessel with argon to 50-60 psig. The Fischer-Porter vessel and dip tube are rinsed with additional toluene (30 g). The reaction mixture is stirred for 2.0 h at 60° C. and is then allowed to cool to ambient temperature while the gases in the headspace are vented.

After the pressure is released, the reaction mixture is transferred to a round-bottom flask containing bleaching clay (Pure-Flo® B80 CG clay, product of Oil-Dri Corporation of America, 2% w/w SBO, 58 g) and a magnetic stir bar. The reaction mixture is stirred at 85° C. under argon. After 2 h, during which time any remaining 1-butene is allowed to vent, the reaction mixture cools to 40° C. and is filtered through a glass frit. An aliquot of the product mixture is transesterified with 1% w/w NaOMe in methanol at 60° C. By gas chromatography (GC), it contains: methyl 9-decenoate (22 wt. %), methyl 9-dodecenoate (16 wt. %), dimethyl 9-octadecenedioate (3 wt. %), and methyl 9-octadecenoate (3 wt. %).

The results compare favorably with calculated yields for a hypothetical equilibrium mixture: methyl 9-decenoate (23.4 wt. %), methyl 9-dodecenoate (17.9 wt/%), dimethyl 9-octadecenedioate (3.7 wt. %), and methyl 9-octadecenoate (1.8 wt. %).

Example 1B

The procedure of Example 1A is generally followed with 1.73 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (18 wt. %), dimethyl 9-octadecenedioate (2 wt. %), and methyl 9-octadecenoate (2 wt. %).

Example 1C

The procedure of Example 1A is generally followed with 1.75 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (17 wt. %), dimethyl 9-octadecenedioate (3 wt. %), and methyl 9-octadecenoate (2 wt. %).

Example 1D

The procedure of Example 1A is generally followed with 2.2 kg SBO and 3 mol 1-butene/SBO double bond. Additionally, the toluene used to transfer the catalyst (60 g) is replaced with SBO. An aliquot of the product mixture is transesterified with sodium methoxide in methanol as described above. The products (by GC) are: methyl 9-decenoate (25 wt. %), methyl 9-dodecenoate (18 wt. %), dimethyl 9-octadecenedioate (3 wt. %), and methyl 9-octadecenoate (1 wt. %).

Example 1E

Separation of Olefins from Modified Triglyceride

A 12-L round-bottom flask equipped with a magnetic stir bar, heating mantle, and temperature controller is charged with the combined reaction products from Examples 1A-1D (8.42 kg). A cooling condenser with a vacuum inlet is attached to the middle neck of the flask and a receiving flask is connected to the condenser. Volatile hydrocarbons (olefins) are removed from the reaction product by vacuum distillation. Pot temperature: 22° C.-130° C.; distillation head temperature: 19° C.-70° C.; pressure: 2000-160 ptorr. After removing the volatile hydrocarbons, 5.34 kg of non-volatile residue remains. An aliquot of the non-volatile product mixture is transesterified with sodium methoxide in methanol as described above. The products (by GC) are: methyl 9-decenoate (32 wt. %), methyl 9-dodecenoate (23 wt. %), dimethyl 9-octadecenedioate (4 wt. %), and methyl 9-octadecenoate (5 wt. %). This mixture is also called "UTG-0." (An analogous product made from palm oil is called "PUTG-0.")

Example 1F

Methanolysis of Modified Triglyceride

A 12-L round-bottom flask fitted with a magnetic stir bar, condenser, heating mantle, temperature probe, and gas adapter is charged with sodium methoxide in methanol (1% w/w, 4.0 L) and the non-volatile product mixture produced in Example 1E (5.34 kg). The resulting light-yellow heterogeneous mixture is stirred at 60° C. After 1 h, the mixture turns homogeneous and has an orange color (pH=11). After 2 h of reaction, the mixture is cooled to ambient temperature and two layers form. The organic phase is washed with aqueous methanol (50% v/v, 2×3 L), separated, and neutralized by washing with glacial acetic acid in methanol (1 mol HOAc/mol NaOMe) to pH=6.5. Yield: 5.03 kg.

Example 1G

Isolation of Methyl Ester Feedstocks

A 12-L round-bottom flask fitted with a magnetic stirrer, packed column, and temperature controller is charged with the methyl ester mixture produced in example 1F (5.03 kg), and the flask is placed in a heating mantle. The glass column is 2"×36" and contains 0.16" Pro-Pak™ stainless-steel saddles (Cannon Instrument Co.). The column is attached to a fractional distillation head to which a 1-L pre-weighed flask is fitted for collecting fractions. Distillation is performed under vacuum (100-120 µtorr). A reflux ratio of 1:3 is used to isolate methyl 9-decenoate ("C10-0") and methyl 9-dodecenoate ("C12-0"). Samples collected during the distillation, distillation conditions, and the composition of the fractions (by GC) are shown in Table 1. A reflux ratio of 1:3 refers to 1 drop collected for every 3 drops sent back to the distillation column. Combining appropriate fractions yields methyl 9-decenoate (1.46 kg, 99.7% pure) and methyl 9-dodecenoate (0.55 kg, >98% pure).

TABLE 1

Isolation of C10-0 and C12-0 by Distillation

| Distillation Fractions # | Head temp. (° C.) | Pot temp. (° C.) | Vacuum (µtorr) | Weight (g) | C10-0 (wt %) | C12-0 (wt %) |
|---|---|---|---|---|---|---|
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Amide Syntheses:
C10-28: C10 MEA Amide

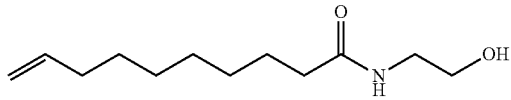

A round-bottom flask equipped with nitrogen sparge, thermocouple, heating mantle, agitator, and Dean-Stark trap is charged with methyl ester feedstock C10-0 (129.8 g, 0.703 mol) and monoethanolamine ("MEA," 43.8 g, 0.718 mol). The mixture is heated to 60° C. Sodium methoxide (2.22 mL of 30 wt. % solution in methanol, 0.012 mol) is added to the flask, and the reaction exotherms to ~80° C. The mixture is then heated to 100° C. and held for 2.5 h. The reactor is cooled to 90° C. and the Dean-Stark trap is removed. Vacuum is applied incrementally to 20 mm Hg over 0.5 h. Vacuum was held at 20 mm Hg for 0.5 h, then at 1.4 mm Hg for 1.0 h to remove residual methanol. $^1$H NMR spectroscopy indicates reasonably complete conversion as is judged readily by the loss of methyl ester CH$_3$O— signal at about 3.6 ppm. Free MEA, determined by titration, is 0.61%.
C12-25: C12 DMA Amide

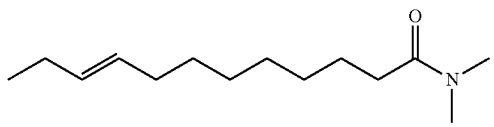 [SMILES: CC/C=C/CCCCCCCC(=O)N(C)C]

A round-bottom flask is charged with methyl ester feedstock C12-0 (900.0 g, 4.22 mol) and the material is heated to 60° C. The reactor is sealed and vacuum is applied for 0.5 h to dry/degas the feedstock. The reactor is backfilled with nitrogen, and then sodium methoxide (30 g of 30% solution in methanol) is added via syringe. A static vacuum (–30" Hg) is established, and then dimethylamine ("DMA," 190.3 g, 4.22 mol) is slowly added via sub-surface dip tube. When the pressure equalizes, the reactor is opened to nitrogen overhead and the temperature is increased 70° C. for 1.0 h. The reactor is then cooled to room temperature and the DMA addition is discontinued. Heating resumes to 80° C. and DMA is slowly introduced via sub-surface sparge and held for 2.0 h. The temperature is then increased to 90° C. and held for 1.0 h. $^1$H NMR spectroscopy indicates >98% conversion. The mixture is cooled to 75° C. and full vacuum is applied to strip methanol and excess DMA. The catalyst is quenched by adding 50% aqueous sulfuric acid (16.3 g) and the mixture is stirred vigorously for 10 min. Deionized water (200 mL) is added and all of the contents are transferred to a bottom-draining vessel. The aqueous layer is removed. The wash is repeated with 300 mL and then 150 mL of deionized water. Approximately 50 mL of 20% NaCl solution is added and the mixture settles overnight. The lower layer is removed and the product is transferred back to the reactor. The product is heated to 75° C. and vacuum is applied to remove residual water. The amide is recovered by vacuum distillation at 120° C. The amide fraction is placed under full vacuum at 135° C. until the ester content is below 1%. Final ester content: 0.7%. Yield: 875 g (91.9%).
C12-30: C12 MEA Amide

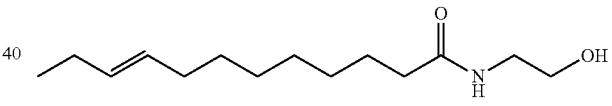

The procedure used to make C10-28 is generally followed using methyl ester feedstock C12-0 (125.1 g, 0.596 mol), monoethanolamine (37.2 g, 0.608 mol), and sodium methoxide (2.14 mL of 30 wt % solution in methanol, 0.011 mol). $^1$H NMR spectroscopy indicates reasonably complete conversion. Free MEA: 0.71%.
C12-31: C12 DEA Amide

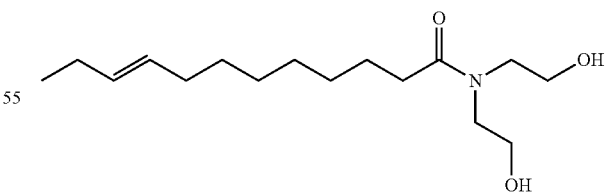

The procedure used to make C10-28 is generally followed using methyl ester feedstock C12-0 (124.7 g, 0.587 mol), diethanolamine (62.9 g, 0.598 mol), and sodium methoxide (2.14 mL of 30 wt % solution in methanol, 0.011 mol). Reaction time is increased to 9.5 h at 100° C. $^1$H NMR spectroscopy indicates reasonably complete conversion. Free DEA: 4.99%.

C12-38: C12 MIPA Amide

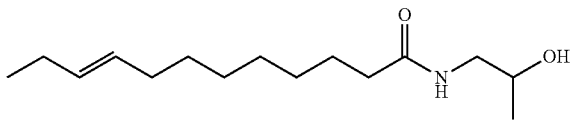 [SMILES: CC/C=C/CCCCCCCC(=O)NCC(C)O]

The procedure used to make C10-28 is generally followed using methyl ester feedstock C12-0 (126.7 g, 0.604 mol), monoisopropanolamine (46.3 g, 0.616 mol), and sodium methoxide (2.17 mL of 30 wt % solution in methanol, 0.012 mol). $^1$H NMR spectroscopy indicates that the product has the expected structure. Free MIPA: 1.15%.

C10-25: C10 DMA Amide

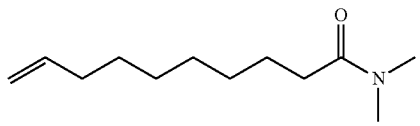

A round-bottom flask is charged with methyl ester feedstock C10-0 (235 g) and the mixture is degassed with nitrogen. Sodium methoxide (5 g of 30% solution in methanol) is added via syringe and the mixture is stirred for 5 min. Dimethylamine (67 g) is slowly added via sub-surface dip tube. After the addition, the mixture is heated to 60° C. and held overnight. The amide, C10-25, is recovered via vacuum distillation (120° C., 20 mm Hg). Yield: 241.2 g (96.3%). Iodine value=128.9 g I$_2$/100 g sample.

$^1$H NMR (CDCl$_3$), δ (ppm)=5.8 (CH$_2$=CH—); 4.9 (CH$_2$=CH—); 2.8-3.0 (—C(O)—N(CH$_3$)$_2$); 2.25 (—CH$_2$—C(O)—). Ester content (by $^1$H NMR): 0.54%.

C10-27: C10 DEA Amide

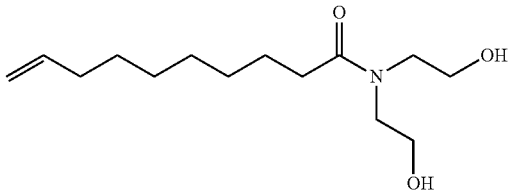 [SMILES: C=CCCCCCCCC(=O)N(CCO)CCO]

The procedure used to make C10-28 is generally followed using methyl ester feedstock C10-0 (96.8 g, 0.524 mol), diethanolamine (53.2 g, 0.506 mol), and sodium methoxide (1.68 mL of 30 wt % solution in methanol, 0.0080 mol). $^1$H NMR spectroscopy indicates reasonably complete conversion. Free DEA: 5.54%.

Imidazoline Syntheses:

Imidazolines are synthesized from fatty acids (C10-36 and C12-39) and DETA or AEEA as described below.

C10-36: C10 Fatty Acid

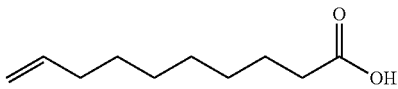

Methyl ester C10-0 (390.2 g) is charged to a round-bottom flask equipped with an overhead stirrer, and the contents are warmed to 70° C. Potassium hydroxide (16% solution in glycerin, 523 g) is added. The mixture is heated to 100° C. and additional KOH pellets (35.10 g) are added. After stirring 17 h, gas chromatography indicates ~94% conversion to the fatty acid. Additional KOH (10 g) is added, and stirring continues at 100° C. for 4 h. Conversion by GC is >97%. The mixture stirs at 100° C. for another 4 h, and is then cooled to 80° C. Water (400 mL) and 30% sulfuric acid solution (500 mL) are added, and the mixture stirs for 1 h. The aqueous phase is then removed. Water (500 mL) is added, and heating/stirring resumes (to 80° C.) for 0.5 h. The aqueous phase is again removed. The water washing process is repeated two more times (2×500 mL). The crude fatty acid product is stripped under vacuum at 80° C. for 2 h to remove water and is used without further purification. Yield: 357 g.

C10-12: C10 DETA Amide

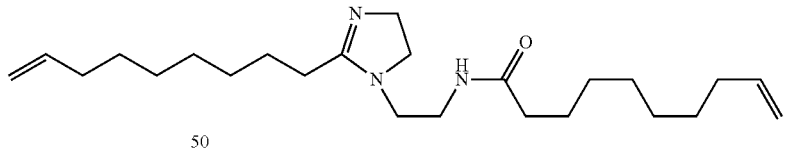

A round-bottom flask is charged with fatty acid C10-36 (310 g) and the feedstock is degassed with nitrogen. Diethylenetriamine ("DETA," 62.6 g) is added and the mixture is heated from 130° C. to 170° C. over 4 h and stirred (170 rpm) under a flow of nitrogen (175 mL/min.). After 18 h, titration reveals 0.097 meq/g of free fatty acid. The temperature is increased to 200° C. for 4 h. Titration indicates 96% ring closure to form C10-12.

C10-15: C10 AEEA Ester

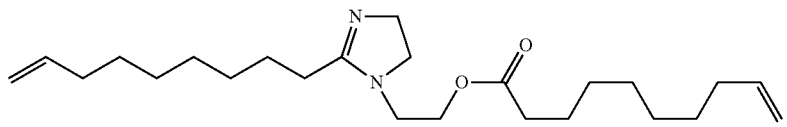 [SMILES: C=CCCCCCCCC(=O)OCCN1CCN=C1CCCCCCCC=C]

A round-bottom flask is charged with half of the required amount of fatty acid C10-36 (117.5 g) and the feedstock is degassed with nitrogen. 2-Aminoethyl-ethanolamine ("AEEA," 69.5 g) and xylene (20.8 g) are added and the mixture is heated rapidly to 180° C. Water is removed using a Dean-Stark trap and a sub-surface nitrogen sparge (175 mL/min.) at atmospheric pressure. The mixture is heated for 18 h at 180° C. The remaining fatty acid (117.5 g) is added, and temperature is increased to 190° C. After 6 h, titration indicates a complete reaction. Yield: 94.6%.

C12-39: C12 Fatty Acid

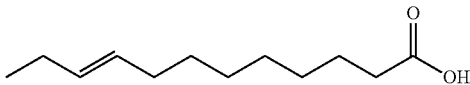

The procedure used to make fatty acid C10-36 is generally followed. Thus, the flask is charged with glycerin (749 g) and KOH pellets (142 g) and heated to 100° C. until the KOH dissolves. After cooling to 75° C., methyl ester C12-0 (384 g, 2.084 mol) is added, and the mixture is heated to 120° C. Heating continues for 4 h. GC indicates complete conversion. After cooling to 85° C., 30% $H_2SO_4$ (1000 mL) is added in one portion. The two-phase mixture stirs at 85° C. for 0.5 h, and the aqueous phase is removed. The fatty acid (C12-39) is washed with water (3×1000 mL) at 85° C. and dried as described previously. It is used without further purification. Yield: 346.2 g.

C12-15: C12 AEEA Ester

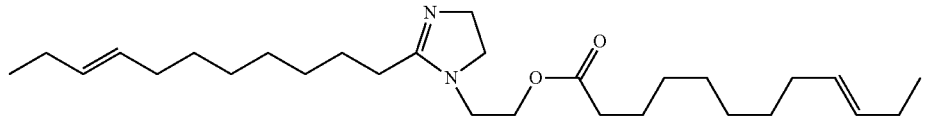 [SMILES: CC/C=C/CCCCCCCC(=O)OCCN1CCN=C1CCCCCCC/C=C/CC]

A round-bottom flask is charged with the fatty acid C12-39 (250.0 g) and the feedstock is degassed with nitrogen. AEEA (63.9 g) is added and the mixture is heated from 130° C. to 170° C. over 4 h and stirred (170 rpm) under a flow of nitrogen (175 mL/min.). After 22 h, titration of free fatty acid indicates 93% conversion to C12-15.

C12-12: C12 DETA Amide

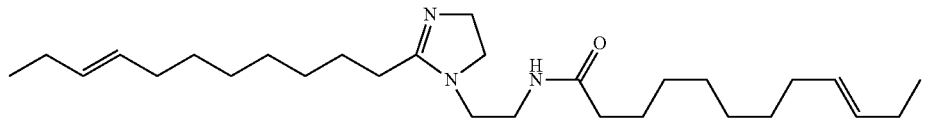 [SMILES: CC/C=C/CCCCCCCC(=O)NCCN1CCN=C1CCCCCCC/C=C/CC]

Methyl 9-dodecenoate ("C12-0," 273.3 g), DABCO (0.3450 g), and DETA (66.48 g) are charged to a round-bottom flask, and the liquid mixture is sparged with nitrogen (175 mL/min). The mixture is heated from 100° C. to 170° C. over 2 h at atmospheric pressure. After 4.5 h at 170° C., a vacuum (90 mm Hg) is applied, and the mixture is heated for an additional 6 h. The resulting distillate (44.3 g) includes about 2 g of DETA. Additional DETA (2 g) is added to the reactor, and heating continues at 170° C. for 5 h at 400 mm Hg. The temperature is raised to 200° C. at improved vacuum (50 mm Hg). After 4 h, there is no distillate. p-Toluenesulfonic acid is added (to induce ring closure to the imidazoline), and the mixture is reheated (200° C., 50 mm Hg) for 22 h. Analysis by titration shows that ring closure is 81%.

Quaternization of Imidazolines

C10-13: C10 DETA Quat

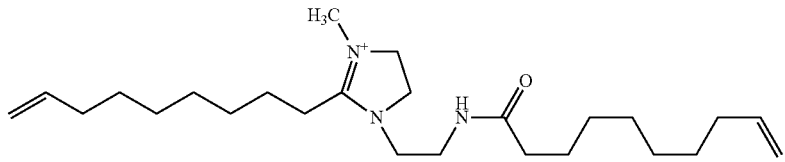

A round-bottom flask is charged with imidazoline C10-12 (202.1 g), which is degassed with nitrogen and heated to 75° C. Dimethyl sulfate ("DMS," 60.6 g) is added via addition funnel with cooling to keep the reaction temperature at ~80° C. After the DMS addition is complete, the mixture is held at 80° C. for 1 h. Free amine (by perchloric acid titration): 0.067 meq/g. Isopropyl alcohol (IPA) (13.9 g) is added, and the mixture is heated to 85° C. for 1 h to destroy any unreacted DMS.

C10-16: C10 AEEA Quat

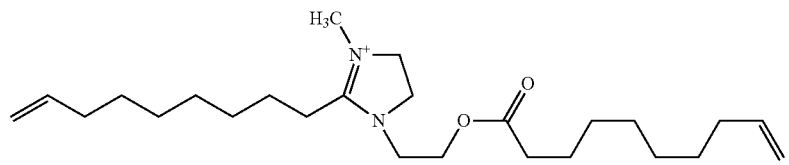 [SMILES: C=CCCCCCCCC(=O)OCCN1CC[N+](C)=C1CCCCCCCC=C]

The procedure used to make C10-13 is generally followed with imidazoline C10-15 (109.6 g), DMS (12.15 g), and IPA (6.4 g). Free amine: 0.08 meq/g.

C12-16: C12 AEEA Quat

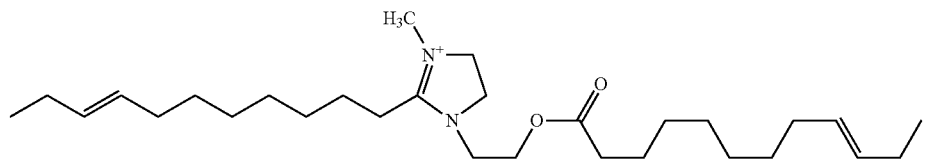 [SMILES: CC/C=C/CCCCCCCC(=O)OCCN1CC[N+](C)=C1CCCCCCC/C=C/CC]

The procedure used to make C10-13 is generally followed with imidazoline C12-15 (112.3 g), DMS (11.0 g), and IPA (6.5 g). DMS is added in two portions (10.8 g and 0.2 g) with a total heating time of 3 h at 80° C. Free amine: 0.067 meq/g.

C12-13: C12 DETA Quat

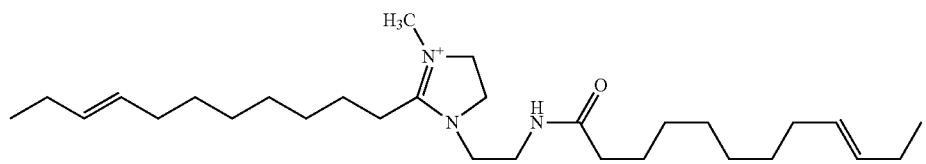 [SMILES: CC/C=C/CCCCCCCC(=O)NCCN1CC[N+](C)=C1CCCCCCC/C=C/CC]

A flask equipped with condensor, nitrogen inlet, thermocouple, and port for an addition flask is charged with imidazoline C12-12 (212.1 g). The contents are heated to 80° C., and DMS (59.3 g) is added via the addition flask with a target perchloric acid titer (PAT) value of 0.065. The temperature is raised to 85° C., and stirring continues for 1 h. A sample is removed and titrated for PAT (found: 0.045). Isopropyl alcohol (30.4 g) is added, and the mixture is stirred for 1 h.

Sulfitation Reactions:

C10-14: C10 DETA Quat Sulfonate

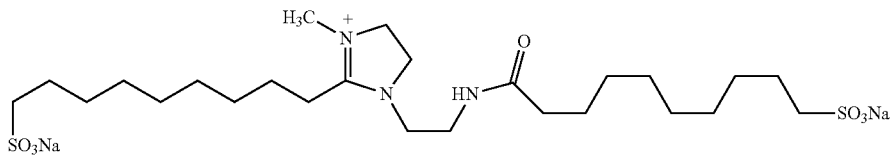

A round-bottom flask is charged with sodium metabisulfite (78.48 g) and deionized water (176 g). The pH is adjusted to 6.6 with 50% sodium hydroxide. The mixture is heated to 75° C. and isopropyl alcohol (117 g) and t-butylperoxybenzoate (TBB, 0.2 mL) are added at once. After 10 min., olefin C10-13 (117.4 g) is added, followed by the remaining TBB (0.58 mL). After 1 h, the pH rises to 7.7 and is reduced to 6.6 by the addition of $SO_2$ gas. After 0.5 h, the pH rises to 7.1 and is reduced to 6.5 with $SO_2$. The mixture stirs at 75° C. for 1.5 days, adjusting the pH two more times with $SO_2$ to 6.5. The $^1H$ NMR spectrum shows the disappearance of the olefin signals, indicating a complete conversion to the disulfonate.

C12-14: C12 DETA Quat Sulfonate

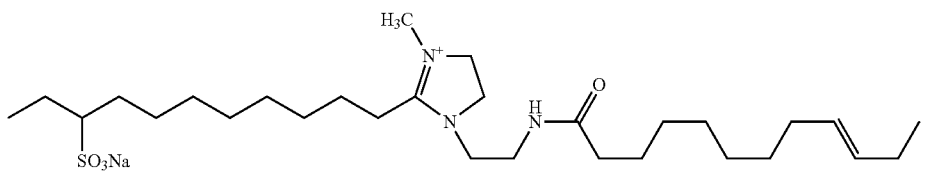

The C12 DETA quat (C12-13, 126.1 g), IPA (126.1 g), and t-butylperoxybenzoate (2.5 g) are charged to a round-bottom flask. The mixture is heated to 75° C. A solution of sodium metabisulfite (37.5 g), sodium sulfite (7.2 g), deionized water (190.0 g), and t-butylperoxybenzoate (1.2 g) is charged to an addition funnel, and then added dropwise to the reaction mixture, which is held at 75° C. for 16 h. IPA is removed via rotary evaporation. The $^1H$ NMR spectrum suggests 75% conversion. Moisture content is adjusted to ~50% by adding water. (Note: the structure indicated above suggests single-site sulfonation, but the skilled person appreciates that at least some of the product with be the result of sulfonation at both carbon-carbon double bonds.)

C12-29: C12 DMA Amide Sulfonate

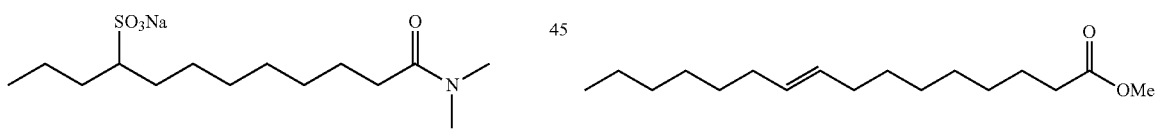

Sodium metabisulfite (43.9 g), sodium sulfite (1.45 g), isopropyl alcohol (656.5 g), amide C12-25 (101.0 g), and water (606 g) are charged to a round-bottom flask and the pH is adjusted to 6.5 with caustic. t-Butylperoxybenzoate (TBB, 0.43 mL) is added and the mixture is heated to 75° C. After 16 h, conversion is about 50% by $^1H$ NMR. More TBB (0.44 mL) is added and the mixture is heated at 75° C. for 8 h. After 2 days at room temperature, more TBB (0.2 mL) is added and the mixture is heated to 75° C. The pH (5.8) is adjusted to 7.2 with caustic and then with $SO_2$ to 7.0. After 16 h, conversion is about 70%. IPA is removed and the resulting two layers are separated. The top phase (unreacted amide, ~52 g) is removed. An NMR spectrum of the bottom phase shows the ratio of sulfonate product to starting olefin is 94:6 mol %.

C10-26: C10 DMA Sulfonate

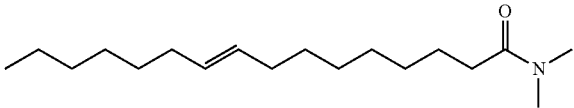 [SMILES: CCCCCC/C=C/CCCCCCCC(=O)N(C)C]

Sulfur trioxide (23.6 g) is added dropwise to unsaturated amide C10-25 (48.6 g) in a vaporizer at a rate effective to maintain the reaction temperature between 35-40° C. Initial fuming in the reactor headspace is minimal. About halfway through the $SO_3$ addition, the reaction product becomes too viscous to stir adequately. The reactor is fitted with a dry ice/acetone trap and the product is diluted with methylene chloride (50 mL) to aid agitation. The reaction temperature is maintained between 20° C.-25° C. Additional methylene chloride (20 mL) is added during the $SO_3$ addition to maintain fluidity. At the end of the addition, the reactor is purged with nitrogen for 5 min. Total addition time: 45 min. The yellow-brown product (104.76 g) is transferred to a round-bottom flask, and solvent is removed under vacuum (~40° C., 2 h). The resulting sulfonic acid is digested at 45° C. for 30 min. Yield: 71.4 g.

Aqueous sodium hydroxide (75 g of 10.7% solution) is added to the dried sulfonic acid. The pH is adjusted as necessary. Once dissolved, the mixture is transferred to a flask equipped with mechanical stirring. Water (78.4 g) and aqueous NaOH (24.6 g of 50% solution) are added. The mixture is heated to 95° C. overnight, maintaining pH=7 with 50% aq. NaOH solution, and then cooled.

Preparation of Methyl 9-Hexadecenoate ("C16-0") Feedstock

The procedures of Example 1A is generally followed except that 1-octene is cross-metathesized with soybean oil instead of 1-butene. Combined reaction products are then stripped as described in Example 1E to remove the more volatile unsaturated hydrocarbon fraction from the modified oil fraction. The procedure of Example 1F is used to convert the modified oil fraction to a methyl ester mixture that includes methyl 9-hexadecenoate. Fractional distillation at reduced pressure is used to isolate the desired product, methyl 9-hexadecenoate from other methyl esters.

C16-14: C16 DMA Amide

Methyl ester C16-0 (502 g, 1.8 mol) is charged to a vessel equipped with mechanical stirring, thermocouple, vacuum gauge and distillation sidearm. The material is heated to 50° C. and full vacuum is applied for 30 min. to dry and degas the system. The vessel is backfilled with nitrogen and sodium methoxide (30% solution in methanol, 20 g) is charged via syringe. The mixture is stirred 5 min. and then the pressure is reduced to approximately −25" Hg. The vessel is sealed under static vacuum and addition of dimethylamine (DMA) via sub-surface dip-tube is initiated. When the pressure in the vessel equalizes, the distillation sidearm is connected to a water trap/bubbler and charging continues at atmospheric pressure, adjusting the rate of addition to minimize blow-by (indicated by bubbling in scrubber). When a slight excess of DMA has been charged, the vessel is stirred for 3 h at 60° C. under nitrogen. $^1$H NMR analysis indicates complete consumption of the methyl ester, and the mixture is cooled to room temperature overnight. The mixture is reheated to 65° C. and vacuum-stripped to remove excess DMA and MeOH. When stripping is complete, the vessel is backfilled with nitrogen. Concentrated HCl is added in portions until a moistened pH test strip indicates a slightly acidic pH. After stirring 15 min., the neutralized mixture is washed with water (3×200 mL), adding 20% NaCl as needed to facilitate phase separation. The washed product is heated to 65° C. and vacuum is slowly applied to remove water. When stripping is complete, the vessel is backfilled with nitrogen and the stripped product is filtered through a plug of silica gel on a glass frit to remove a fine precipitate. The product remains hazy, and it is diluted with ethyl acetate and filtered again through a pad of Celite, giving a clear yellow liquid. Volatiles are removed via rotary evaporator, then under high vacuum, affording dimethylamide C16-14 as a light yellow oil (509.4 g; 96.8% yield). $^1$H NMR analysis is consistent with the target structure and shows 0.8% methyl ester remaining. Further analysis shows: moisture: 0.04%; iodine value: 89.3 g I$_2$/100 g sample.

Feedstock Synthesis

Preparation of Dimethyl 9-Octadecene-1,18-dioate ("Mix-0" or "C18-0")

Eight samples of methyl 9-dodecenoate (10.6 g each, see Table 2) are warmed to 50° C. and degassed with argon for 30 min. A metathesis catalyst ([1,3-bis-(2,4,6-trimethylphenyl)- 2-imidazolidinylidene]dichlororuthenium(3-methyl-2-butenylidene)-(tricyclohexylphosphine), product of Materia) is added to the methyl 9-dodecenoate (amount indicated in Table 2) and vacuum is applied to provide a pressure of <1 mm Hg. The reaction mixture is allowed to self-metathesize for the time reported. Analysis by gas chromatography indicates that dimethyl 9-octadecene-1,18-dioate is produced in the yields reported in Table 2. "Mix-0" is an 80:20 trans-/cis-isomer mixture obtained from the reaction mixture. Crystallization provides the all-trans-isomer feed, "C18-0."

TABLE 2

Self-Metathesis of Methyl 9-Dodecanoate

| Sample | Catalyst Loading (ppm mol/mol)* | Reaction Time (h) | C18-0 (GC Area %) |
|---|---|---|---|
| A | 100 | 3 | 83.5 |
| B | 50 | 3 | 82.5 |
| C | 25 | 3 | 83.0 |
| D | 10 | 3 | 66.2 |
| E | 15 | 4 | 90.0 |
| F | 13 | 4 | 89.9 |
| G | 10 | 4 | 81.1 |
| H | 5 | 4 | 50.9 |

*ppm mol catalyst/mol methyl 9-dodecenoate

Amides from C18 Diacids:

MIX-39: C18 DiDMA Amide (80:20 trans-/cis-)

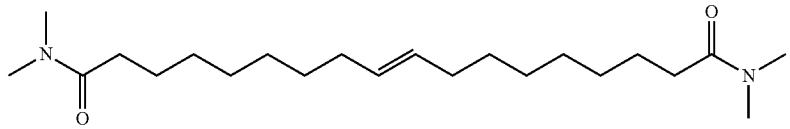

A round-bottom flask is charged with methyl ester Mix-0 (250.0 g, 0.73 mol) and the feedstock is heated to 50° C. Sodium methoxide (10 g of 30% solution in methanol) is added via syringe. The reactor is sealed and a static vacuum (−25" Hg) is established. Dimethylamine (80 g) is slowly added via sub-surface dip tube. The reaction temperature is increased to 55° C. and held for ~9 h. Residual ester (by $^1$H NMR): <0.8%. Full vacuum is applied to strip excess methanol and DMA. The catalyst is quenched by adding 50% aqueous sulfuric acid (5.4 g). Vacuum is applied to remove water. The product is diluted in chloroform and filtered through Celite. Chloroform is removed via rotary evaporation and the product is dried overnight under full vacuum. $^1$H NMR indicates reasonably complete conversion of methyl ester groups

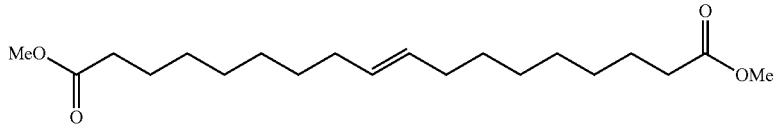 [SMILES: COC(=O)CCCCCCC/C=C/CCCCCCCC(=O)OC]

to dimethyl amide groups as evidenced by negligible methyl ester CH$_3$O— signal at about 3.6 ppm and the expected amide CH$_3$ singlets at 2.9-3 ppm.

C18-41: C18 DiMEA Amide (100% Trans-)

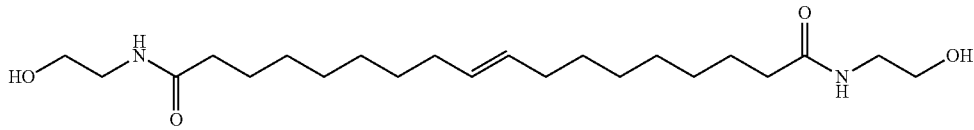 [SMILES: O=C(CCCCCCC/C=C/CCCCCCCC(=O)NCCO)NCCO]

A round-bottom flask equipped with nitrogen sparge, thermocouple, heating mantle, agitator, and Dean-Stark trap is charged with dibasic ester C18-0 (129.9 g, 0.763 mol) and monoethanolamine (47.5 g, 0.778 mol). The mixture is heated to 60° C. Sodium methoxide (2.23 mL of 30 wt. % solution in methanol, 0.012 mol) is added to the flask. The reactor is heated to 70° C., the temperature spikes to ~90° C., and the mixture forms a solid mass. The reactor is heated to 155° C., and after the solid melts, the reactor is held at 155° C. for 1 h. The trap is removed and vacuum is improved incrementally to 50 mm Hg over 0.5 h, then held for 1.5 h. The product is flaked by pouring the molten amide onto a sheet of aluminum foil, allowing it to harden, and then breaking it off of the foil. $^1$H NMR indicates reasonably complete conversion. Free MEA (by titration): 1.70%.

MIX-41: C18 DiMEA Amide (80:20 trans-/cis-)

The apparatus used to make C18-41 is charged with dibasic ester Mix-0 (129.9 g, 0.760 mol) and monoethanolamine (47.4 g, 0.776 mol). The mixture is heated to 150° C. and held overnight. Additional monoethanolamine (1.0 g) is added and reacted for 1 h. Total reaction time: 24 h. Full vacuum is applied for 3.0 h to remove residual methanol and excess MEA. The product is flaked as described above. $^1$H NMR indicates reasonably complete conversion. Free MEA: 0.92%.

C18-42: C18 DiDEA Amide (100% trans-)

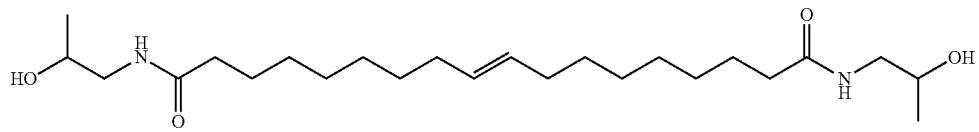

The procedure used to make C18-41 is generally followed with dibasic ester C18-0 (106.1 g, 0.623 mol) and diethanolamine (66.8 g, 0.636 mol). The mixture is heated to 60° C., and sodium methoxide (1.82 mL of 30 wt % solution in methanol, 0.010 mol) is added. The mixture is heated to 100° C. and held for 8.5 h. After cooling to 70° C., full vacuum is applied for 0.5 h to remove residual methanol. $^1$H NMR indicates reasonably complete conversion. Free DEA: 6.71%.

MIX-42: C18 DiDEA Amide (80:20 trans-/cis-)

The procedure used to make C18-42 is generally followed with dibasic ester Mix-0 (109.7 g, 0.644 mol) and diethanolamine (69.1 g, 0.657 mol). The mixture is heated at 100° C. for 5 h, then cooled and stripped as described above. $^1$H NMR indicates reasonably complete conversion. Free DEA: 6.71%.

C18-66: C18 DiMIPA Amide (100% trans-)

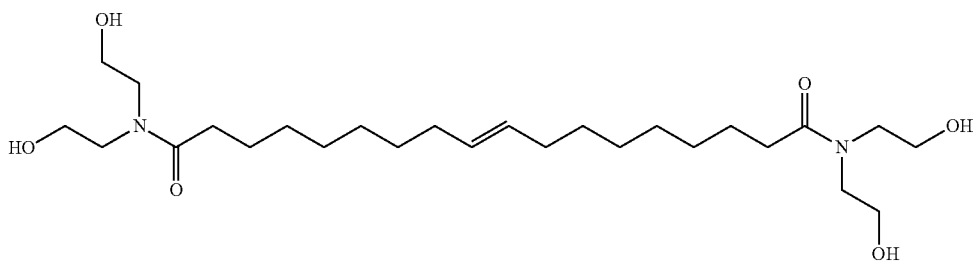 [SMILES: O=C(CCCCCCC/C=C/CCCCCCCC(=O)N(CCO)CCO)N(CCO)CCO]

The apparatus used to make C18-41 is charged with monoisopropanolamine (54.1 g, 0.720 mol), which is heated to 80° C. Dibasic ester C18-0 (120.2 g, 0.706 mol) is charged to the reactor via a powder funnel while increasing the reactor temperature to 100° C. A nitrogen sparge is used to assist removal of methanol. The reactor temperature is increased to 130° C. and held for 5 h, allowed to cool, then reheated to 135° C. and held overnight. After vacuum stripping, the product is flaked by pouring the molten amide onto foil as described earlier. $^1$H NMR indicates reasonably complete conversion. Free MIPA: 0.33%.

MIX-66: C18 DiMIPA Amide (80:20 trans-/cis-)

The procedure used to make C18-66 is generally followed with dibasic ester MIX-0 (128.1 g, 0.750 mol) and monoisopropanolamine (57.5 g, 0.765 mol). The mixture is heated to 130-135° C. and held overnight. $^1$H NMR spectroscopy indicates reasonably complete conversion. Free MIPA: 0.65%.

Imidazolines and Derivatives from C18 Dibasic Esters:
MIX-21: C18 DiDETA (80:20 trans-/cis-)

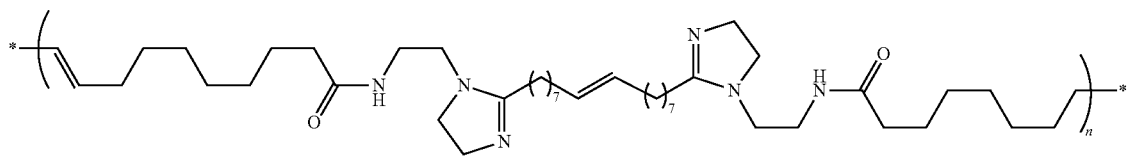

A round-bottom flask is charged with dibasic ester C18-0 (267 g) and the feedstock is degassed with nitrogen. DETA (131 g) and DABCO (0.24 g) are added and the mixture is heated to 140° C. Methanol is collected via a Dean-Stark trap with nitrogen sparge. After 18 h, reaction temperature is increased to 197° C. for 4 h. Vacuum (10 mm Hg) is applied and p-toluenesulfonic acid (0.5 g) is added. Temperature is reduced to 175° C. and vacuum is replaced by a nitrogen sparge. Heating continues for 18 h. Analysis by titration shows that ring closure is 77%.

MIX-22: C18 DiDETA DiQuat (80:20 trans-1 cis-)

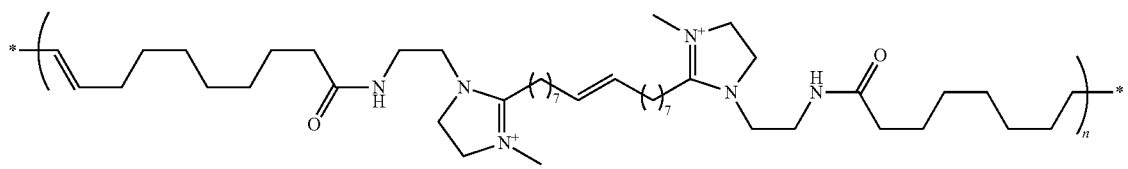

Mix-21 (79.5 g) is charged to a flask equipped with condenser, nitrogen inlet, thermocouple, and addition flask. The imidazoline is heated to 65° C. and DMS (35.8 g) is added. Methanol (34 g) is added to decrease viscosity. After 2 h, the temperature is increased to 78° C. and held for 3 h. Titration confirms the disappearance of DMS from the reaction mixture and the desired product in good yield.

MIX-23: C18 DiDETA DiQuat Sulfonate

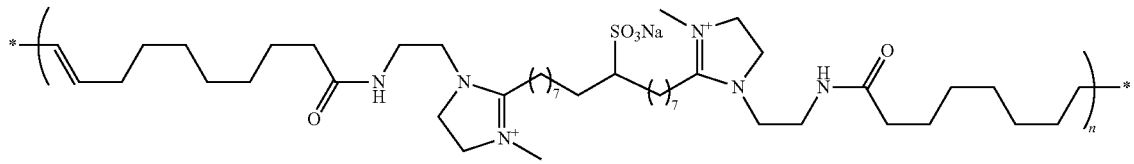

A round-bottom flask is charged with diquat Mix-22 (127.9 g), isopropyl alcohol (100 g), and water (300 g). Sodium bisulfate (40.98 g), sodium sulfite (2.7 g), and t-butylperoxybenzoate are added, and the mixture is heated to 75° C. and held overnight. $^1$H NMR analysis confirms complete disappearance of the olefin protons. The isopropyl alcohol is removed via rotary evaporation to obtain the final product.

MIX-69: C18 Ester/Acid (80:20 trans-/cis-)

The half-acid/ester Mix-69 is prepared from the dibasic ester Mix-0 (used as received) as described in *Organic Syntheses: Col. Vol. IV* (1963) 635. Thus, Mix-0 (1 kg) is added to methanol (~9 L) and the mixture is stirred mechanically. In a separate vessel, Ba(OH)$_2$ (274.4 g) is dissolved in methanol (~4 L), and the solution is added in portions over 2 h to the stirred diester solution, resulting in the formation of a white precipitate. The solid is isolated by filtration, washed several times with methanol, and dried in air. The solid is then transferred to a 12-L reaction vessel and slurried in ethyl acetate (~3.5 L). Aqueous HCl (32%, Aldrich, 1248.6 g), is added in portions to the stirred slurry, resulting in dissolution of the solid and formation of a clear solution. The solution is washed three times with water, and the aqueous layers are removed and collected in a separate vessel. The combined aqueous layers are extracted once with ethyl acetate, and the organic phase is combined with the washed product solution. The mixture is dried (Na$_2$SC$_4$), filtered, and concentrated via rotary evaporator. Thorough drying under high vacuum gives a waxy, crystalline solid upon cooling (655 g, ~70% yield). Analysis of the product (following derivatization) by gas chromatography shows that it contains 94% acid/ester and 6% diacid. Quantitative $^{13}$C NMR shows an 86:14 trans:cis isomer ratio.

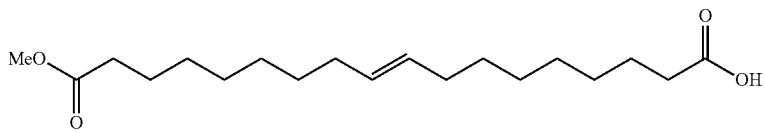 [SMILES: COC(=O)CCCCCCC/C=C/CCCCCCCC(=O)O]

MIX-59: C18 Ester DMA Amide

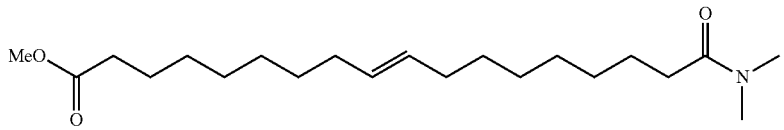 [SMILES: COC(=O)CCCCCCC/C=C/CCCCCCCC(=O)N(C)C]

The mixed acid/ester (Mix-69, 315.2 g) is converted to the acid chloride/ester by reaction with a slight excess of thionyl chloride (SOCl$_2$, 1.2 eq., 147.5 g) in chloroform solution, and the product is isolated by removal of the solvent and excess SOCl$_2$ under reduced pressure. NMR analysis of the isolated product shows essentially quantitative conversion to the acid chloride/ester, and the material is used without further purification.

The acid chloride/ester is diluted with CHCl$_3$ (250 mL) in the same 1-L reaction vessel equipped with mechanical stirrer, nitrogen inlet, stainless steel dipleg, and thermocouple. The mixture is warmed to 40° C. and dimethylamine (DMA) is introduced slowly via sub-surface sparging through the stainless steel dipleg. During the addition, the temperature rises moderately and is maintained at a maximum of 50° C. by external cooling as required. The DMA addition is discontinued when slightly more than 2 molar equivalents have been introduced, and the mixture stirs at 50° C. for 1 h. The vessel is then equipped with a distillation sidearm and dry ice-cooled trap, and excess DMA and CHCl$_3$ are removed by gentle application of vacuum. Volatiles are condensed in the trap, and vacuum is increased in increments until full vacuum is achieved. Full vacuum is maintained for 30 min., and then the apparatus is backfilled with nitrogen. The dark, viscous liquid thus obtained is diluted with ethyl acetate (EtOAc, 500 mL), causing precipitation of a fine solid. The solid is removed by filtration, and the hygroscopic solid is washed with additional EtOAc (2×250 mL). The deep red filtrate is evaporated to dryness via rotary evaporator, affording a deep red oil with moderate viscosity. The oil is taken up in an equivalent volume of EtOAc, and the solution is filtered through a plug of silica gel, resulting in a lightening of the color. The filtrate is then evaporated to dryness via rotovap and dried thoroughly under high vacuum, giving a red oil (332.1 g; 98.7% yield). $^1$H NMR analysis of the product is consistent with the target structure (δ 3.6 ppm, s, 3H, ester —OCH$_3$; δ 3.0 ppm, 2 s, 6H, amide N(CH$_3$)$_2$). Iodine value: 70.7 g I$_2$/100 g sample.

C18-26: C18 DiDMAPA Amide (100% trans-)

A round-bottom flask equipped with a mechanical stirrer is charged with diester C18-0 (545.6 g) and DMAPA (343.3 g). A Dean-Stark trap is attached, and sodium methoxide (20 g of 30 wt % solution in MeOH) is added. The temperature is raised to 110° C. over 1.5 h, and methanol is collected. The temperature is increased to 150° C. in increments as the distillation slows. The mixture is held at 150° C. for 6.5 hours and then cooled to room temperature. $^1$H NMR analysis indicates a minor amount of unreacted methyl ester. The mixture is heated to 180° C. for several hours and additional DMAPA and sodium methoxide are added. The mixture is cooled and neutralized with concentrated hydrochloric acid. When the mixture has cooled to 90° C., deionized water is added slowly with vigorous agitation, resulting in precipitation of the amide to afford a slurry. Solids are isolated by vacuum filtration and washed with water. The solid product, all-trans amide C18-26, is dried under vacuum. Yield: 92.2%. $^1$H NMR (CDCl$_3$) confirms formation of the amide, based on disappearance of the methyl ester peak at 3.65 ppm and appearance of the DMAPA CH$_2$ signals at 3.31, 2.12, and 1.62 ppm and the N(CH$_3$)$_2$ at 2.20 ppm.

C18-68: C18 DiDMAPA Amide Sulfonate

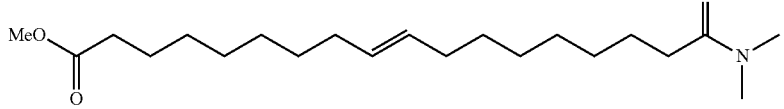

DiDMAPA amidoamine C18-26 (82.9 g) is added to isopropyl alcohol (IPA, 500 g), and the mixture is heated to 60° C. and stirred, giving a homogeneous solution. Sodium sulfite (9.3 g) is dissolved in water (250 g), and the solution is added to the amidoamine solution. The pH is adjusted from 9.2 to 6.5 with gaseous SO$_2$ and t-butylperoxybenzoate (TBB, 0.90 mL) is added. The mixture is stirred at 75° C., and more IPA (50 g) is added to help solubility. Eventually, the mixture thickens and more IPA (50 g) and water (50 g) are added. The mixture stirs overnight. Water (75 g) and more TBB (0.25 mL) are added to the cloudy mixture. Analysis by $^1$H NMR after several hours indicates 50% conversion. The mixture stirs overnight, and further analysis shows 59% conversion. A slow C$_2$ sparge is introduced to drive off IPA and the temperature is raised to 80° C. After approximately 6 h, heating is discontinued and the mixture stirs at room temperature over the weekend. Analysis shows 97% conversion. Residual IPA is stripped to give the sulfonate, C18-68. Moisture: 62.6%; inorganic sulfate: 7.28%.

Modified Triglyceride Based on Soybean Oil ("MTG-0")

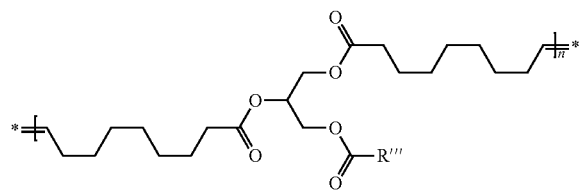

The procedures of Examples 1A and 1E are generally followed except that 1-butene is omitted.
Mod. Triglyceride from Cross-Metathesis of Soybean Oil and 1-Butene ("UTG-0")

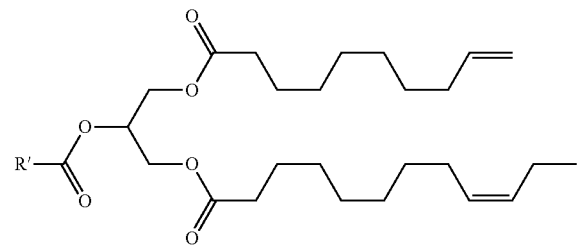

Unsaturated Triglycerides
(C10 and C12 enriched, also containing C16 and C18 Saturates)

The procedures of Examples 1A and 1E are generally followed to produce UTG-0 from soybean oil and 1-butene.
Modified Triglyceride Based on Palm Oil ("PMTG-0")

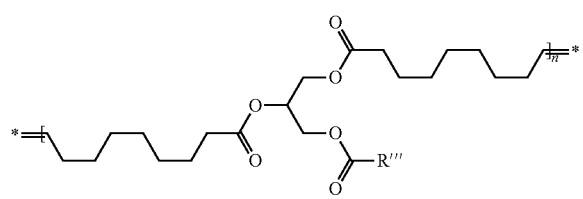

The procedure used to make MTG-0 is followed, except that palm oil is used instead of soybean oil.

Mod. Triglyceride From Cross-Metathesis of Palm Oil and 1-Butene ("PUTG-0")

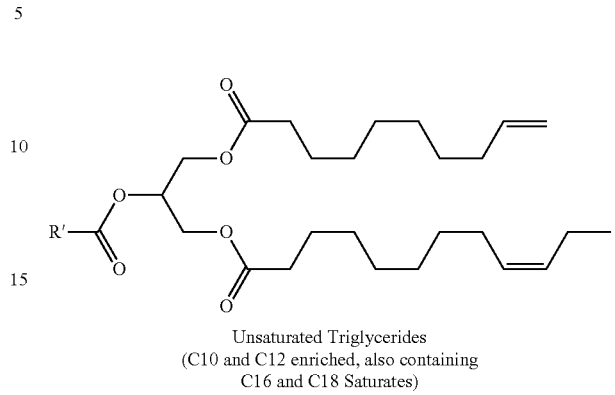

Unsaturated Triglycerides
(C10 and C12 enriched, also containing C16 and C18 Saturates)

The procedure used to make UTG-0 is followed, except that palm oil is used instead of soybean oil.

MTG-0 Feedstock Derivatives

TABLE 3

Summary of Modified Triglyceride Products

|  | Soybean Oil | | Palm Oil | |
| --- | --- | --- | --- | --- |
|  | Self-met. MTG-0 | X-met. UTG-0 | Self-met. PMTG-0 | X-met. PUTG-0 |
| DMA Amide | MTG-15 | UTG-15 | PMTG-15 | PUTG-15 |
| DEA Amide | MTG-16 | UTG-16 | PMTG-16 | PUTG-16 |
| MEA Amide | MTG-17 | UTG-17 | PMTG-17 | PUTG-17 |
| MIPA Amide | MTG-18 | UTG-18 | PMTG-18 | PUTG-18 |

DMA = dimethylamine; DEA = diethanolamine; MEA = monoethanolamine; MIPA = monoisopropanolamine Fatty amides are prepared from modified triglycerides (MTG-0, PMTG-0) or unsaturated triglycerides (UTG-0, PUTG-0). Details of the preparation for the MTG products (MTG-15, -16, -17, and -18) appear below. The corresponding PMTG products are prepared analogously. Details of the preparation for the PUTG products (PUTG-15, -16, -17, and -18) also appear below, and the corresponding UTG products are prepared analogously.

MTG-15: MTG DMA Amide

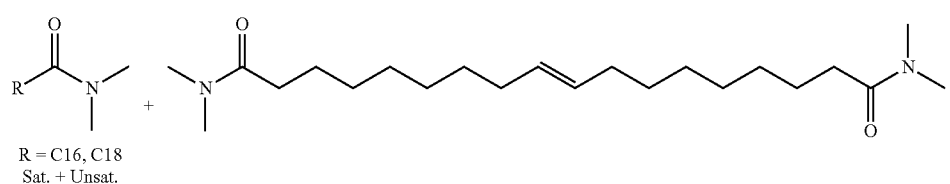

R = C16, C18
Sat. + Unsat.

A round-bottom flask is charged with MTG-0 (175.0 g, 0.71 mol) and the feedstock is heated to 60° C. The reactor is sealed and vacuum is applied to dry/degas the feedstock. The reactor is backfilled with nitrogen, and then sodium methoxide (7.5 g of 30% solution in methanol) is added via syringe. The reactor temperature is increased to 90° C. A static vacuum (−30″ Hg) is established, and dimethylamine (87 g) is slowly added via sub-surface dip tube. When the pressure in the reactor equalizes, it is opened to nitrogen overhead and the temperature is increased to 110° C. for 3.0 h. Reaction progress is checked by infrared spectroscopy (IR). The temperature is increased to 150° C. and held for an additional 8.5 h. IR indicates a reasonably complete reaction.

The catalyst is quenched by adding 50% aqueous sulfuric acid (4.1 g). Deionized water (100 mL) is added, and the mixture is stirred vigorously for ~15 min. The reactor contents are washed with water with heat applied to aid phase separation. Aqueous sulfuric acid is added until the aqueous phase tests acidic. Aqueous NaCl solution (20%) is also used to aid phase separation. The amide product is washed twice more with aqueous brine and is then returned to the reaction vessel. The reactor is heated to 70° C. and full vacuum is applied for 0.5 h to remove residual water. The warm product is then filtered through silica gel on a glass frit.

MTG-16: MTG DEA Amide

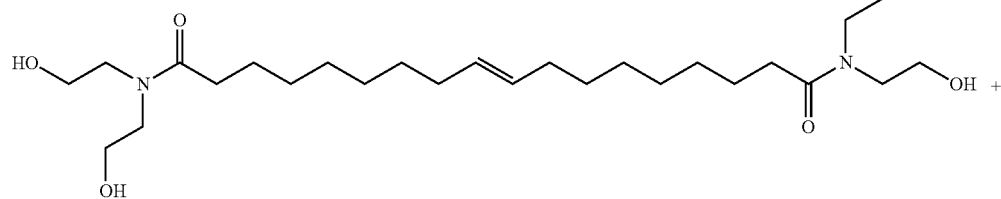

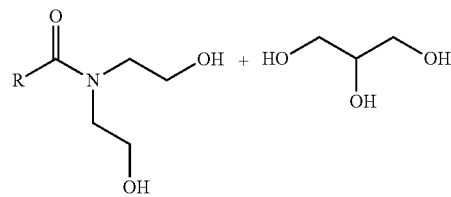

R = C16, C18 Sat. + Unsat.

A round-bottom flask equipped with nitrogen inlet, thermocouple, heating mantle, and agitator is charged with MTG-0 (133.8 g, 0.487 mol) and the feedstock is heated to 65° C. Sodium borohydride (0.067 g, 0.0018 mol) is added, and the contents are stirred at 65° C. for 1 h. Diethanolamine (52.2 g, 0.497 mol) and sodium methoxide (2.29 mL of 30 wt % solution in methanol, 0.012 mol) are charged to the mixture. After addition of the catalyst, the reaction exotherms to ~80° C. Once the exotherm subsides, the reactor is heated to 90-95° C. and held overnight. Full vacuum is applied for 5.0 h. $^1$H NMR indicates reasonably complete conversion. Free DEA: 3.89%.

MTG-17: MTG MEA Amide

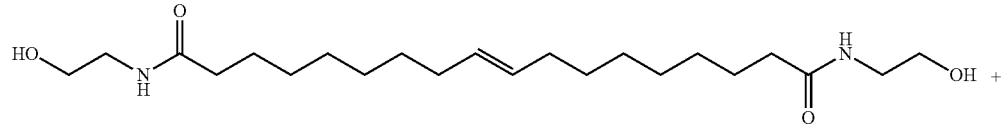

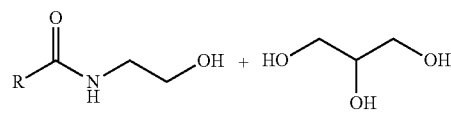

R = C16, C18 Sat. + Unsat.

The procedure used to make MTG-16 is generally followed with MTG-0 (134.2 g, 0.488 mol), sodium borohydride (0.067 g, 0.0018 mol), monoethanolamine (30.4 g, 0.498 mol) and sodium methoxide (2.30 mL of 30 wt % solution in methanol, 0.012 mol). Full vacuum was applied for 1.0 h to strip residual free amine. $^1$H NMR indicates reasonably complete conversion. Free MEA: 0.53%.

MTG-18: MTG MIPA Amide

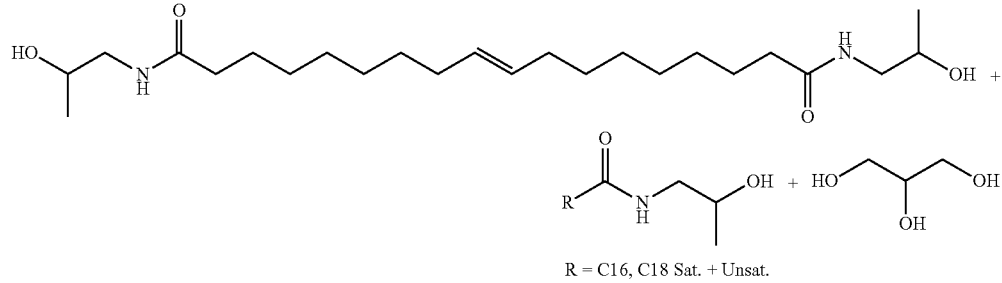

The procedure used to make MTG-16 is generally followed with MTG-0 (130.5 g, 0.527 mol), sodium borohydride (0.065 g, 0.0017 mol), monoisopropanolamine (40.35 g, 0.537 mol) and sodium methoxide (2.24 mL of 30 wt % solution in methanol, 0.012 mol). Full vacuum was applied for 1.0 h to strip residual free amine. $^1$H NMR indicates reasonably complete conversion. Free MIPA: 0.64%.

PUTG-15: PUTG DMA Amide

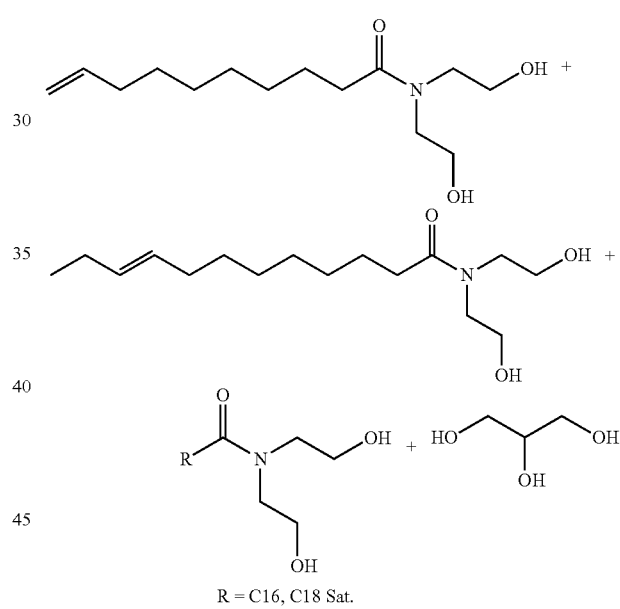

The procedure used to make MTG-15 is generally followed using PUTG-0 (250.0 g, 0.91 mol), sodium methoxide (5.0 g of 30% solution in methanol), and dimethylamine (43 g). When the pressure in the reactor equalizes, the reactor is opened to nitrogen overhead and the mixture was held at 80° C. overnight. IR analysis shows significant glyceride remaining. The temperature is increased to 120° C. and DMA addition is continued via sub-surface sparge for ~4 h. The temperature is then increased to 140° C. and DMA addition continues for 2 h. The reaction mixture is cooled to room temperature. Total DMA charged: 43 g. The reactor is reheated to 140° C. and more sodium methoxide (5 g of 30% solution in methanol) is added. DMA addition continues for 2.0 h. The temperature is reduced to 80° C. and held for 7 h.

The mixture is warmed to 50° C. and deionized water (100 mL) is added. The catalyst is quenched by adding 50% aqueous sulfuric acid (9.1 g) and the mixture is worked up as described earlier. $^1$H NMR indicates reasonably complete conversion.

PUTG-16: PUTG DEA Amide

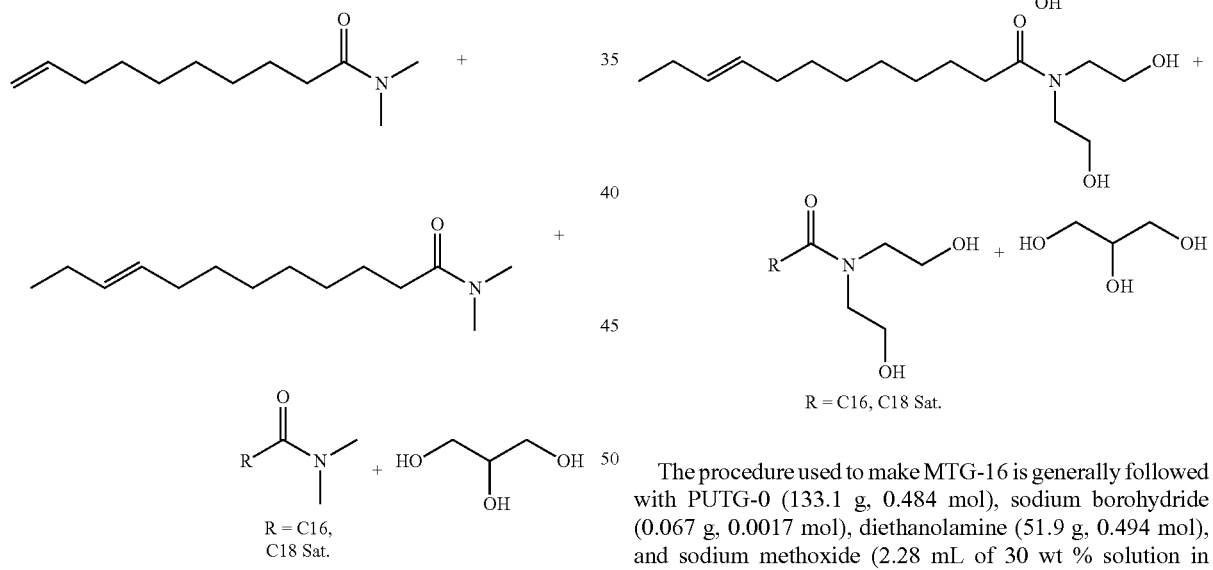

The procedure used to make MTG-16 is generally followed with PUTG-0 (133.1 g, 0.484 mol), sodium borohydride (0.067 g, 0.0017 mol), diethanolamine (51.9 g, 0.494 mol), and sodium methoxide (2.28 mL of 30 wt % solution in methanol, 0.012 mol). $^1$H NMR indicates reasonably complete conversion. Free DEA: 2.04%.

PUTG-17: PUTG MEA Amide

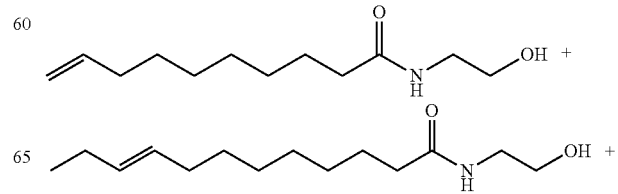

-continued

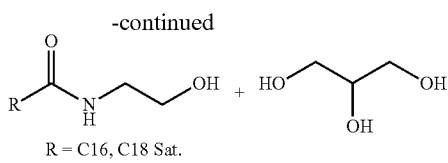

R = C16, C18 Sat.

The procedure used to make MTG-16 is generally followed with PUTG-0 (136.6 g, 0.497 mol), sodium borohydride (0.068 g, 0.0018 mol), monoethanolamine (31.0 g, 0.507 mol), and sodium methoxide (2.34 mL of 30 wt % solution in methanol, 0.013 mol). $^1$H NMR indicates reasonably complete conversion. Free MEA: 0.96%.

PUTG-18: PUTG MIPA Amide

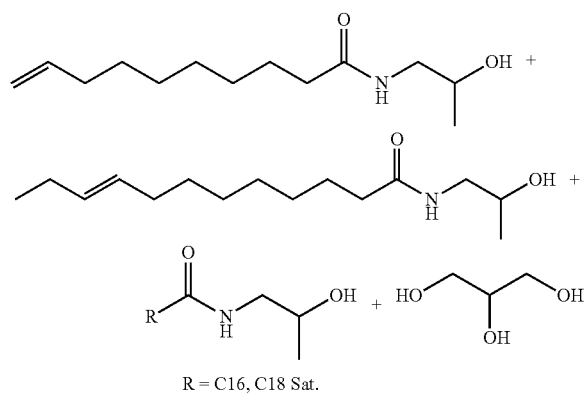

R = C16, C18 Sat.

The procedure used to make MTG-16 is generally followed with PUTG-0 (136.1 g, 0.495 mol), sodium borohydride (0.068 g, 0.0018 mol), monoisopropanolamine (38.0 g, 0.505 mol), and sodium methoxide (2.34 mL of 30 wt % solution in methanol, 0.013 mol). $^1$H NMR indicates reasonably complete conversion. Free MIPA: 0.90%.

Agricultural Products: Anionic Emulsifiers

Anionic surfactant samples contain a relatively high amount of water (>20%) and are prepared as oil-in-water (EW) concentrates. These are tested against controls containing a standard surfactant or a blank. Enough is formulated to test two water hardnesses (34 ppm and 1000 ppm) for each of the three samples.

Sample Preparation:

Pyraflufen (97.8% active, 0.30 g) is combined and with Stepan® C-25 (methyl caprylate/caprate, 7.20 g), and N-methyl-2-pyrrolidone (1.20 g), and the mixture is stirred magnetically until dissolved. In a separate container, Toximul® 8242 (castor oil ethoxylate, POE 40, product of Stepan) 0.96 g), Ninex® MT-630F (fatty acid ethoxylate, POE 30, Stepan, 0.19 g), Ninex® MT-615 (fatty acid ethoxylate, POE 15, Stepan, 0.17 g), Aromatic 150 solvent (ExxonMobil, 0.37 g), and the anionic sample to be tested (0.71 g) are blended. If needed, the anionic sample is melted in an oven at 50-60° C. prior to combining with the other surfactants. When the pyraflufen has dissolved, the entire surfactant blend is added and magnetically stirred until homogeneous. Deionized water (0.90 g) is slowly added with mixing to prevent gelling. Turbidity changes are noted and recorded.

Control 1 Sample:

The same procedure is followed except that the anionic sample is replaced with Ninate® 60 L (calcium alkylbenzenesulfonate, Stepan, 0.71 g).

Control 2 Sample:

No Ninate 60 L (or anionic sample) is included, and the Aromatic 150 amount is increased to 1.08 g.

Emulsion Stability Testing

ASTM E1116-98 (2008) is modified as follows. Flat-bottomed, 100-mL graduated cylinders are charged with 34 ppm or 1000 ppm water (95 mL). A Mohr pipette is used to feed EW concentrate to each cylinder. Cylinders are stoppered and inverted ten times, then allowed to stand for 0.5, 1, and 24 h while recording stability at each time as type and % separation.

Spontaneity is recorded according to the following criteria: (1) poor: very thin emulsion cloud with major separation of oil droplets; (2) fair: thin emulsion cloud with minor separation of oil droplets; (3) good: thin emulsion cloud reaches the bottom of the cylinder without separation of any type; (4) excellent: thick emulsion cloud reaches the bottom of the cylinder without separation of any type.

Results are provided in Table 4. The three samples indicated below are rated "good" overall as an anionic surfactant.

TABLE 4

Performance as an Anionic Emulsifier: % Separation

|  | 34 ppm water | | | 1000 ppm water | | |
| --- | --- | --- | --- | --- | --- | --- |
|  | Spont. | 1 h | 24 h | Spont. | 1 h | 24 h |
| Control 1 | G | <0.2 C | 1.3 C | G | <0.2 C | 1.3 C |
| Control 2 | F | 4 C | 4.4 C | F | 4 C | 4.4 C |
| C10-14 | F+ | 3 C | 3.8 C | F+ | 2.5 C | 3 C |
| C12-14 | F | 4 C | 4 C | F | 3 C | 3.2 C |
| C18-68 | F | 3.9 C | 5 C | F− | 3 C | 4.8 C |

"C" denotes separation in the form of a cream, not a creamy oil or an oil.
"Tr" denotes trace of oil observed.
"O" denotes oil separated
"Spont." = spontaneity or bloom, rated as E (excellent), G (good), F (fair), P (poor).
Control 1 = native anionic;
Control 2 = no anionic emulsifier.

Agricultural Products: Nonionic Emulsifiers

Nonionic samples contain a low amount of water (<1%) and are prepared as emulsifiable concentrates (EC) with three pesticides using two different solvent systems. In the aromatic solvent series, the nonionic sample replaces Toximul® 8240 (castor oil ethoxylate, 36 POE, Stepan), and in the Hallcomid™ (N,N-dimethylcaprylamide/N,N-dimethylcapramide, Stepan) solvent series, the nonionic sample replaces Ninex® MT-630F. The amounts prepared are enough to test two water hardnesses (34 ppm and 1000 ppm) for each of the three samples.

Aromatic Solvent Series.

Sample preparation: Ninate® 60E (calcium alkylbenzenesulfonate, Stepan) and the test sample are stirred until homogeneous. If needed, the nonionic surfactant is melted in an oven at 50-60° C. prior to its combination with Ninate 60E. Controls 1-3 are made by using Toximul 8240 in the amounts indicated instead of the nonionic sample.

Formulations:
1. Bifenthrin, 240 g/L (2.99 g), Aromatic 100 (ExxonMobil, 8.05 g), Ninate 60E (0.38 g), and nonionic sample or Toximul 8240 (0.58 g).
2. 2,4-D ester, 480 g/L (8.90 g), Exxsol® D-110 (ExxonMobil, 2.50 g), Ninate 60E (0.36 g), and nonionic sample or Toximul 8240 (0.24 g).
3. Tebuconazole, 360 g/L (4.45 g), N-methyl-2-pyrrolidone (6.35 g), Ninate 60E (0.48 g), nonionic sample or Toximul 8240 (0.72 g).

Hallcomid Solvent Series.

Sample preparation: The surfactants are combined and stirred until homogeneous, with the nonionic sample melted if needed prior to combination. Controls 1-3 are made by using Ninex MT-630F in the amounts indicated instead of the nonionic sample.

Formulations:
1. Bifenthrin, 240 g/L (2.99 g), Hallcomid M-8-10 (8.29 g), Ninate 60E (0.09 g), Toximul 8320 (0.22 g), Toximul 8242 (0.29 g), and nonionic sample or Ninex MT-630F (0.13 g).
2. 2,4-D diester, 480 g/L (8.90 g), Hallcomid M-8-10 (2.38 g), Ninate 60E (0.09 g), Toximul 8320 (0.22 g), Toximul 8242 (0.29 g), and nonionic sample or Ninex MT-630F (0.13 g).
3. Tebuconazole, 360 g/L (4.45 g), Hallcomid M-8-10 (6.83 g), Ninate 60E (0.09 g), Toximul 8320 (0.22 g), Toximul 8242 (0.29 g), and nonionic sample or Ninex MT-630F (0.13 g).

Emulsion Stability Testing

ASTM E1116-98 (2008) is modified as follows. Flat-bottomed, 100-mL graduated cylinders are charged with 34 ppm or 1000 ppm water (95 mL). A Mohr pipette is used to feed EW concentrate to each cylinder. Cylinders are stoppered and inverted ten times, then allowed to stand for 0.5, 1, and 24 h while recording stability at each time as type and % separation. Spontaneity is evaluated as described for testing anionic emulsifiers.

Results with both solvent systems are provided in Table 5. Based on the overall test results, C10-27 is rated "good" as a nonionic surfactant.

DF-500, and DF-600 (all products of Stepan Company), and each is optionally tested with and without a nonionic or anionic wetting agent.

A screening sample is prepared as shown below for each active. Wetting agents, clays, and various additives are included or excluded from the screening process as needed. The weight percent of pesticide ("technical material") in the formulation depends on the desired active level of the final product. The active level chosen is similar to other products on the market. If this is a new active ingredient, then the highest active level is used.

Samples are evaluated in waters of varying hardness, in this case 342 ppm and 1000 ppm. The initial evaluations are performed at ambient temperature. Other temperatures can be evaluated as desired. The 342 ppm water is made by dissolving anhydrous calcium chloride (0.304 g) and magnesium chloride hexahydrate (0.139 g) in deionized water and diluting to 1 L. The 1000 ppm water is made similarly using 0.89 g of calcium chloride and 0.40 g of magnesium chloride hexahydrate.

Technical material (60-92.5 wt. %), wetting agent (0.5-1.0 wt. % when used), silica (0.5-1.0 wt. %), and clay (balance) are blended in a suitable container. The blend is milled to a particle size of at least a d(90) of <20μ using a hammer and air/jet mills as needed. Test dispersant (0.1 g) is added to test water (50 mL) in a beaker and stirred 1-2 min. Milled powder containing the technical material (1.0 g) is added to the dispersant solution and stirred until all powder is wet (2-5 min.). The mixture is transferred to a 100-mL cylinder using additional test water for rinsing the beaker and is then diluted to volume. The cylinder is stoppered and inverted ten times, then

TABLE 5

| | | Performance as a Nonionic Surfactant | | | | |
|---|---|---|---|---|---|---|
| | | 34 ppm water | | | 1000 ppm water | |
| | pesticide | Spon. | 1 h | 24 h | Spon. | 1 h | 24 h |
| | | Aromatic Solvent | | | | |
| Control 1 | Bifenthrin | G | 2.5 C | 3 C, 1 CO, 1 O | G | 2 C | 2 C, 1 CO, 1 O |
| | 2,4-D | F | 2.5 C | 5 O | F | 4.8 O | 5 O |
| | Tebucon. | F | 1.6 C | 3 C, 2 OC | G | 1.8 C | 1.5 C, 2.5 OC |
| C10-27 | Bifenthrin | P | 3 C, 1 O | 5 C, 3 O | P | 13 C | 11 C, 2 O |
| | 2,4-D | P | 1 O | Tr C, 4 O | P | 4 CO | 1 CO, 4.5 O |
| | Tebucon. | P | 2 OC | 3 CO | P | 2.8 OC | 3 CO |
| | | Hallcomid Solvent | | | | |
| Control 2 | Bifenthrin | G | 6 OC | 6 O | G | 6 OC | 6 O |
| | 2,4-D | F | 5 C | 9.8 C | F | 5.5 C | 9.5 C |
| | Tebucon. | G | 1 C | 4 C | G | 1 C | 4 C, 4 CO |
| C10-27 | Bifenthrin | F | 11.5 C | 3 CO, 2 O | F | 9 CO | 3 CO, 2 O |
| | 2,4-D | F | 6 C | 9 C | F | 7 C | 8.5 C |
| | Tebucon. | F | 2 C | 5 OC | F | 2 C | 1 O, 4 OC |

Spontaneity: G = good; F = fair; P = poor.
Appearance: C = creamy; CO = creamy oil; O = oil; OC = oily cream; S = sediment; FS = flaky sediment; OS = oily sediment; Tr = trace.
Numbers are amounts in mL.
Control 1 replaces test sample with castor oil ethoxylate (POE: 36).
Control 2 replaces test sample with a fatty acid ethoxylate (POE: 30)

Agricultural Dispersant Screening:

The potential of a composition for use as an agricultural dispersant is evaluated by its performance with five typical pesticide active ingredients: atrazine, chlorothalonil, diuron, imidacloprid and tebuconazole. The performance of each dispersant sample is evaluated in comparison with five standard Stepsperse® dispersants: DF-100, DF-200, DF-400, allowed to stand. Visual inspection is performed at t=0.5, 1.0, 2.0, and 24 hours, and the amount of sediment observed (in mL) is recorded. Trace of sediment="Tr" (see Tables 7 and 8).

Overall results versus the controls are summarized in Table 6; four amides perform at least as well as the controls. Details of the individual tests are reported in Table 7 (wetting agent included) and Table 8 (no wetting agent).

TABLE 6

| Performance as an Agricultural Dispersant | |
|---|---|
| Sample | Rating |
| C12-13 | Superior |
| C10-13 | Good |
| C12-16 | Good |
| Mix-22 | Good |
| Control | Good | mL) and type of separation are recorded after 30 min., 1 h, 2 h, and 24 h. Results of the solubility testing appear in Table 9 below.

Anionic Test Sample:

Paraquat (4.57 g of 43.8% active material) is added to a 20-mL glass vial. An eight to ten mole alkyl phenol ethoxylate surfactant (0.7 g) is added and vigorously mixed for 30 s. Test sample (0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

TABLE 7

Agricultural Dispersants Testing: Nonionic or Anionic Wetting Agent Included
Sedimentation results at 1 h; 24 h (mL)

| | test water, ppm | DF-200 | DF-500 | C10-13 (+anionic) | C12-13 (+anionic) | C12-16 (+nonionic) | Mix-22 (+anionic) |
|---|---|---|---|---|---|---|---|
| Diuron | 342 | 0.25-0.5; 1 | Tr; 1 | 0.25-0.5; 1 | 0.5-1; 1 | — | 0.5-0.75; 1.5 |
| | 1000 | 0.5-1; 1-1.25 | 2-2.5; 2 | 5; 1.75-2 | 0.5-1; 1 | — | 0.5; 1.0 |
| Chlorothalonil | 342 | 0.25; 1.5 | Tr; 1.25 | 0.5-0.75; 1-1.5 | 0.5-1; 1 | — | 1.25; 2.5-2.75 |
| | 1000 | Tr; 1.75 | 5; 3.5 | 0.25-0.5; 1.5-1.75 | 1; 1 | 0.5-1; 1-1.25 | 1.25; 2.5 |
| Imidacloprid | 342 | Tr; 1-1.5 | Tr; 1.5-2 | 3-3.25; 2-2.25 | 1; 2 | — | 0.75-1; 2.25 |
| | 1000 | Tr; 2 | 1-1.5; 3 | 3; 2.5 | 1; 2 | — | 0.75; 2.0 |
| Tebuconazole | 342 | 0; 1 | Tr; 1 | 0; 0.5 | 0.5; 1 | — | 0.25-0.5; 1.0 |
| | 1000 | 0.5-1; 3.5-4 | 12; 5 | 0; 1 | 0.5-1; 1-1.5 | — | 0.25; 1.5 |
| Atrazine | 342 | Tr; 1 | Tr; 1 | 0.25-0.5; 1 | Tr; 1 | — | 0.25; 1.5-1.75 |
| | 1000 | Tr; 2 | 7; 4 | 0.25-0.5; 1.75-2 | Tr-0.25; 1 | 0.25-0.5; 2-2.25 | 0.25-0.5; 1.25 |
| Rating here | | control | control | good | superior | good | good |

TABLE 8

Agricultural Dispersants Testing: No Wetting Agent
Sedimentation results at 1 h; 24 h (mL)

| | test water, ppm | DF-200 | DF-500 | C12-13 | C12-16 |
|---|---|---|---|---|---|
| Diuron | 342 | 1; 2 | 0.5; 1-1.5 | 1; 1.25-1.5 | 0.5-0.75; 1-1.25 |
| | 1000 | 1; 2-2.5 | 0.5-0.75; 2 | 1; 1.5-1.75 | 0.75-1; 1-1.25 |
| Chlorothalonil | 342 | 0.25; 1-1.25 | 0.25; 1-1.25 | 0; 0.5-0.75 | 6; 5 |
| | 1000 | 0.25-0.5; 1.25-1.5 | 2; 3 | 0; 0.75-1 | 5; 4 |
| Imidacloprid | 342 | Tr; 1-1.5 | 0.5-1; 2 | 0.25-0.5; 1 | 1.5-2; 2 |
| | 1000 | Tr; 1-1.5 | 0.5-1; 2-2.5 | 1; 1-1.5 | 0.75-1; 1.5-1.75 |
| Tebuconazole | 342 | Tr; 1.25 | Tr; 1.5 | 1; 1-1.25 | 0.25; 2-2.25 |
| | 1000 | Tr; 3 | Tr; 3 | 10.5; 1-1.25 | 0.75-1; 3 |
| Atrazine | 342 | Tr-0.25; 1-1.5 | 0.5; 1 | 1; 1 | 1; 2-2.25 |
| | 1000 | Tr-0.25; 1-1.5 | 6; 3 | 1; 1-1.25 | 4; 4 |
| Rating here | | control | control | superior | good (inferior for atrazine and chlorothanonil) |

Water-Soluble Herbicide Formulation Testing

Surfactant candidates for water soluble herbicide applications are examined as a replacement for the anionic, nonionic, or anionic/nonionic blend portion and compared to a known industry adjuvant standard for use in paraquat, a water soluble herbicide concentrate formulation. A standard dilution test is conducted whereby the concentrates are diluted in water to determine if solubility is complete.

Control:

Paraquat (9.13 g of 43.8% active material) is added to a 20-mL glass vial. A known industry paraquat adjuvant (2.8 g) is added and vigorously mixed for 30 s. Deionized water (8.07 g) is added, and mixing resumes for 30 s. Standard 342 ppm water (47.5 mL) is added to a 50-mL Nessler cylinder, which is stoppered and equilibrated in a 30° C. water bath. Once the test water equilibrates, the formulated paraquat (2.5 mL) is added by pipette into the cylinder. The cylinder is stoppered and inverted ten times. Solubility is recorded as complete or incomplete. Cylinders are allowed to stand and the amount (in Nonionic Test Sample:

Paraquat (4.57 g of 43.8% active material) is added to a 20-mL glass vial. Test sample (0.7 g) is added and vigorously mixed for 30 s. Sodium linear alkylbenzene sulfonate ("NaLAS," 0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Adjuvant (Anionic/Nonionic) Test Sample:

Paraquat (4.57 g of 43.8% active material) is added to a 20-mL glass vial. Test sample (1.4 g) is added and vigorously mixed for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Criteria for emulsion solubility: Test samples should be as good as or better than the control with no separation after one hour. Three test samples perform as well as or better than the control in the emulsion stability test. Results appear in Table 9.

TABLE 9

Water Soluble Herbicide Formulation:
Emulsion stability, mL separation

| test | Anionic | | | Nonionic | | | Adjuvant | | | |
|---|---|---|---|---|---|---|---|---|---|---|
| sample | sol | 1 h | 24 h | sol | 1 h | 24 h | sol | 1 h | 24 h | Rating |
| C10-14 | S | 0 | 0 | D | Tr | Tr | S | 0 | 0 | good |
| C10-26 | S | 0 | 0 | D | 0.5 | 0.5 | S | 0 | 0 | good |
| C12-29 | S | 0 | 0 | D | 0.5 | 0.5 | S | 0 | 0 | good |

D = dispersable;
S = soluble;
I = insoluble;
Tr = trace
Control result: Solubility: D; 1 h: 0 mL; 24 h: Tr.

Agrichemical Solvent Analysis: Active Solubility

Solvency strength of potential agrichemical solvents is evaluated by identifying the solubility level of four standard pesticides in the solvent by weight percent: 2,4-D acid, imidacloprid, trifluralin and tebuconazole. Testing is performed using a 4-mL vial with a pane magnetic stirrer and an accurately weighed 2 to 2.2-g sample of solvent. The active material is also accurately weighed before addition. Initial amounts of active material are approximately: 2,4-D: 0.3 g; imidacloprid: 0.02 g; trifluralin: 0.5 g; tebuconazole: 0.3 g. Solvent and pesticide active are combined, allowed to mix for 1 h at room temperature, and then inspected for the presence of undissolved active material. Additional active material is added in appropriately small increments until it no longer dissolves completely. This mixture is then stirred for 24 h at room temperature, and if the active has completely dissolved, additional active ingredient is added and the mixture is stirred another 24 h at room temperature. The percent solubility is recorded, and performance is compared with that of a standard agricultural solvent.

When the method outlined above is followed, five amide compositions perform as well as the control in this test, and one (Mix-59) is superior, as is noted in Table 10 below.

TABLE 10

Performance as an Agricultural Solvent

| Sample | Rating |
|---|---|
| C10-25 | Good |
| C12-25 | Good |
| C16-14 | Good |
| Mix-59 | Superior* |
| MTG-15 | Good* |
| UTG-15 | Good |
| Controls | Good |

*Solidifies at close to room temperature

Detailed results appear in Table 11, below:

TABLE 11

Agricultural Solvent Testing

| Solvent | 2,4-D Acid | Imidacloprid | Trifluralin | Tebuconazole |
|---|---|---|---|---|
| C10-25 | 47.3 | 3.0 | 66.0 | 35.3 |
| C12-25 | 41.7 | 2.0 | 61.5 | 31.2 |
| C16-14 | 36.1 | 1.1 | 51.3 | 24.4 |
| Mix-59 (1:1 with control) | 42.3 | 2.1 | 60.6 | 31.8 |
| MTG-15 | 33.6 | 1.0 | 44.4 | 23.6 |
| UTG-15 | 38.0 | 1.0 | 58.5 | 24.6 |
| methyl palmitate/oleate | 11.5 | 0 | 45.0 | 4.5 |
| $C_{12}$-$C_{14}$ dimethylamide | 38.2 | 1.9 | 64.0 | 32.2 |
| N,N-dimethylcapramide | 42.7 | 4.0 | 67.1 | 38.0 |
| methyl laurate | 11.2 | 0.6 | 58.8 | 5.9 |
| methyl caprate/caprylate | 14.8 | 0.6 | 69.9 | 10 |
| aromatic hydrocarbon | 0.6 | 1.0 | 78.9 | 4.2 |
| N-methyl-2-pyrrolidone | 39.5 | 29.3 | 78 | 62.2 |

Hard-Surface Cleaners: Aqueous Degreasers

This test measures the ability of a cleaning product to remove a greasy dirt soil from a white vinyl tile. The test is automated and uses an industry standard Gardner Straight Line Washability Apparatus. A camera and controlled lighting are used to take a live video of the cleaning process. The machine uses a sponge wetted with a known amount of test product. As the machine wipes the sponge across the soiled tile, the video records the result, from which a cleaning percentage can be determined. A total of 10 strokes are made using test formulation diluted 1:32 with water, and cleaning is calculated for each of strokes 1-10 to provide a profile of the cleaning efficiency of the product. The test sample is used as a component of different control formulations depending on whether it anionic, amphoteric, or nonionic.

Anionic Test Samples:

A neutral, dilutable all-purpose cleaner is prepared from propylene glycol n-propyl ether (4.0 g), butyl carbitol (4.0 g), sodium citrate (4.0 g), Bio-Soft® EC-690 ethoxylated alcohol (1.0 g, product of Stepan), test sample (0.29 g if 100% active material), and deionized water (to 100.0 g solution). The control sample for anionic testing replaces the test sample with Stepanol® WA-Extra PCK (sodium lauryl sulfate, Stepan, 1.0 g, nominally 30% active material).

Nonionic and Amphoteric Test Samples:

A neutral, dilutable all-purpose cleaner is prepared from propylene glycol n-propyl ether (4.0 g), butyl carbitol (4.0 g), sodium citrate (4.0 g), Stepanol® WA-Extra PCK (sodium lauryl sulfate, 1.0 g), test sample (0.90 g if 100% active material), and deionized water (to 100.0 g solution). The control sample for nonionic/amphoteric testing replaces the test sample with Bio-Soft® EC-690 (ethoxylated alcohol, Stepan, 1.0 g, nominally 90% active material).

Soil composition (from Gardner ASTM D4488-95 method):

Tiles are soiled with a particulate medium (50 mg) and an oil medium (5 drops). The particulate medium is composed of (in parts by weight) hyperhumus (39), paraffin oil (1), used motor oil (1.5), Portland cement (17.7), silica 1 (8), molacca black (1.5), iron oxide (0.3), bandy black clay (18), stearic acid (2), and oleic acid (2). The oil medium is composed of kerosene (12), Stoddard solvent (12), paraffin oil (1), SAE-10 motor oil (1), Crisco® shortening, product of J.M. Smucker Co. (1), olive oil (3), linoleic acid (3), and squalene (3).

TABLE 12

Control Runs for Gardner Straight Line Washability Test

| | \multicolumn{5}{c}{Ave. % clean after 2, 4, 6, 8, or 10 swipes} | | | | |
|---|---|---|---|---|---|
| | 2 | 4 | 6 | 8 | 10 |
| Control 1 | 52.4 | 59.0 | 62.5 | 62.8 | 63.9 |
| Control 3 | 54.6 | 61.4 | 64.3 | 68.4 | 72.2 |
| Control 5 | 50.8 | 59.2 | 63.9 | 65.3 | 67.1 |
| Control 6 | 51.2 | 57.6 | 62.7 | 62.6 | 66.0 |
| Control 7 | 52.3 | 56.0 | 61.5 | 64.3 | 65.0 |
| Control 18 | 62.2 | 67.6 | 70.4 | 71.7 | 71.7 |
| Control 20 | 65.0 | 70.7 | 72.2 | 73.7 | 74.0 |

TABLE 13

Gardner Straight Line Washability Results
Nonionic (or net charge neutral) or Amphoteric Samples

| Sample | Con. # | Compound class | 2 | 4 | 6 | 8 | 10 | Rating |
|---|---|---|---|---|---|---|---|---|
| C12-14 | 1 | DETA quat sulfonate | 58.0 | 65.7 | 68.5 | 69.0 | 69.4 | superior |
| C10-14 | 6 | DETA quat sulfonate | 59.0 | 65.2 | 65.6 | 67.7 | 67.4 | equal |
| C10-27 | 7 | DEA amide | 53.9 | 56.0 | 58.4 | 62.0 | 65.2 | equal |
| C12-31 | 5 | DEA amide | 57.3 | 64.2 | 67.1 | 69.0 | 69.6 | equal |
| Mix-23 | 20 | C18 diDETA diquat sulfonate | 58.9 | 68.2 | 69.0 | 71.0 | 71.2 | equal |
| Mix-42 | 18 | C18 diDEA amide | 65.6 | 66.6 | 70.8 | 71.5 | 73.3 | equal |
| \multicolumn{9}{c}{Anionic Samples} | | | | | | | | |
| C10-26 | 3 | DMA amide sulfonate | 53.2 | 57.0 | 61.7 | 65.4 | 66.9 | equal |

TABLE 14

Performance as a Solvent in Industrial Degreasers

| Sample | Composition class | Neat | Diluted |
|---|---|---|---|
| C10-25 | DMA amide | superior | superior |
| C12-25 | DMA amide | equal | superior |

Table 13 shows the results of six nonionic or amphoteric test samples (quat sulfonates and amides) and one anionic sample (an amide sulfonate) that performed as well or better than the control in the Gardner straight-line washability test. Control runs are summarized in Table 12.

Industrial Degreaser Formulations

This test measures the ability of a solvent to clean a greasy dirt soil from a white vinyl tile. The soil is the same as used in the Gardner ASTM D4488-95 A5 method, only applied to the tile with a brush. The test consists of placing a drop of the test solvent onto the soiled tile, waiting 10 seconds (neat samples), or 30 seconds (diluted), then adding a second drop adjacent to the first, waiting the prescribed time, adding a third drop, etc. After a few minutes the dropping is stopped and the tile rinsed, photographed, and judged for cleaning versus control neat, and in formulation diluted.

Neat samples are tested versus Steposol® M8-10, a mixture of N,N-dimethylcapramide and N,N-dimethylcaprylamide, product of Stepan.

Diluted samples are made from test actives (5.0 g), Ammonyx® LMDO (lauramidopropylamine oxide, product of Stepan, 10.0 g), and deionized water (q.s. to 100 g). The control for the diluted samples replaces the test actives with Steposol M8-10 (5.0 g).

Results appear in Table 14. Overall, the $C_{10}$-$C_{12}$ amides outperformed the control as a degreaser solvent when tested neat and diluted.

Personal Care: Cleansing Application

Viscosity and mechanical shake foam tests are used to assess the likely value of a particular surfactant as a secondary surfactant in cleansing applications for personal care.

All experimental samples are evaluated for their performance versus a control (cocamide MEA).

Viscosity curves are generated by preparing dilute aqueous solutions of the test material or control (1.5% active content) with 12% active sodium lauryl ether (1) sulfate (SLES-1), then measuring viscosity by means of a Brookfield DV-1+ viscometer. Sodium chloride is added incrementally (1-3 wt. %) and viscosity is recorded as a function of increasing NaCl concentration. A "good" result is a curve that shows a viscosity build comparable to the control sample. A "superior" rating indicates that the sample builds viscosity substantially more rapidly than the control.

Foaming properties are evaluated using a mechanical shake foam test. Aqueous solutions composed of 12% active SLES-1 and the test material or control (1.5% active amide) are prepared. Sample solutions calculated at 0.2% total surfactant active material are thereafter made from the aqueous solutions using 25° C. tap water. A 100.0-g portion of the solution is carefully transferred to a 500-mL graduated cylinder. Castor oil (2.0 g) is added. The cylinder is stoppered and mechanically inverted ten times, then allowed to settle for 15 s. Foam height is recorded. After 5 min., foam height is recorded again. The experiment is repeated without the castor oil. In one set of experiments, the cleansing base contains SLES-1 in both the experimental and control runs. In a second set of experiments, the cleansing base contains another widely used anionic solvent, i.e., a mixture of sodium methyl 2-sulfolaurate and disodium 2-sulfolaurate, instead of SLES-1. A "good" result is recorded when the solution containing the test material results in foam heights that are within +/−25 mL of the control runs. Results >25 mL of the control garner a superior rating; results <25 mL of the control are rated inferior.

Fourteen test materials, identified in Table 15, show good overall performance in both the viscosity and foam tests.

TABLE 15

Personal Care/Secondary Cleaner Viscosity and Shake Foam Test Results

| Sample | Viscosity Build | Foam Tests |
|---|---|---|
| C12-25 | Superior | Good |
| C12-30 | Good | Good |
| C12-31 | Inferior | Good |
| C12-38 | Good | Good |
| C16-14 | Good | Good |
| MTG-15 | Inferior | Good |
| MTG-16 | Inferior | Good |
| MTG-17 | Good | Good |
| PMTG-16 | Good | Good |
| PMTG-17 | Good | Good |
| PMTG-18 | Good | Good |
| PUTG-15 | Good | Good |
| PUTG-17 | Good | Good |
| PUTG-18 | Good | Good |
| Control | Good | Good |

Control = cocamide MEA

Personal Care/Antibacterial Handsoap:
Method to Determine Foam Enhancement Benefit Foam volume, which signals "clean" to consumers, is a desirable attribute in an antibacterial handsoap. Because cationic antibacterial actives are not compatible with anionic surfactants (the best foamers), achieving sufficient foam volume with them is challenging. The method below identifies surfactants that provide more foam volume than cocamidopropylbetaine (actives/actives basis) in an antibacterial handsoap base. Formulation: deionized water (q.s. to 100 wt. %), cocoglucoside (3.0 wt. %), lauramine oxide (3.0 wt. %), benzalkonium chloride (0.1 wt. %), and test molecule or cocamidopropylbetaine (3.0 wt. %).

Solutions are prepared by combining ingredients in the order prescribed above, stirring with a stir bar or mixing gently using an overhead stirrer or manually using a spatula. Heat may be applied if the test molecule is a solid at room temperature. Mixing is maintained to ensure a homogenous solution. The pH is adjusted to 6.5+/−0.5.

Test and control solutions are compared, with and without 2% castor oil, at 0.2% total surfactant active concentration (2.22 g solution to 100 mL with tap water from Lake Michigan, ~150 ppm Ca/Mg hardness) for foam volume using the cylinder inversion test. Initial and delayed (5 min.) measurements are taken.

Rating system: Superior: A result >25 mL over the cocamidopropylbetaine control in both oil and no-oil systems. Good: A result within 25 mL of the cocamido-propylbetaine control in both oil and no-oil systems. Inferior: A result >25 mL below that of the cocamidopropylbetaine control in both oil and no-oil systems.

Three test materials, identified in Table 16, show good overall performance in the antibacterial handsoap tests.

TABLE 16

Performance in Antibacterial Handsoap vs. Control

| Sample | Rating |
|---|---|
| C10-13 | Good |
| C12-13 | Good |
| C12-14 | Good |

Hair Conditioners: Procedure for Evaluation of Wet Combability

Hair tresses (10" lengths, 2-3 g) are prepared using a consistent and uniform hair type (double-bleached, blond). The tresses are collectively shampooed with a 15% active sodium lauryl sulfate solution. Care is taken to avoid excessive tangling during shampooing. The tresses are rinsed clean with 40° C. tap water. The process is repeated to simulate a double shampoo application. The tresses are separated and tagged for testing. The conditioner preparation, whether it be the test material or the control (i.e., the base conditioner) is applied (2.0 cm$^3$) to each clean, wet tress using a syringe. The base conditioner contains cetyl alcohol (2.0%), hydroxyethyl cellulose (0.7%), cetrimonium chloride (1.0%), potassium chloride (0.5%) and water (qs to 100%). Test samples are formulated as a 2 wt. % (actives) additive to the base conditioner.

The conditioner is worked through the hair for one minute with downward finger strokes. The tresses are rinsed thoroughly clean under 40° C. tap water. Excess water is squeezed from each tress to simulate towel-dry hair. The hair is combed through, at first, in the wet state. Ease of combing is evaluated for the test samples and the base conditioner, and qualitative ratings are assigned to the test samples in comparison to the results with base conditioner only. Enhancement of conditioning of the base by the amide additive is the technical success criteria at this stage and is the basis for a superior rating. Equal to lower performance versus the base conditioner earns an inferior rating. Results appear in Table 17.

TABLE 17

Wet Combability Performance in Hair Conditioners

| Sample | Result |
|---|---|
| C12-15 | Superior |
| Base conditioner | Good |

Cold-Water Cleaning Performance of Compaction Laundry Detergents

This method evaluates the overall cold-water (55° F.) cleaning performance of a laundry detergent formula comprising a concentrated blend of anionic and non-ionic surfactants, a builder, $C_{16}$ MES and an experimental sample. The formulations are prepared as described below. The experimental sample is tested for its ability to improve the overall cleaning performance relative to cocamide DEA.

Preparation of Concentrated Blend:

Deionized water (90% of the required total amount) is first combined and mixed at 50° C. with Bio-Soft® S-101 (dodecylbenzene sulfonic acid, 3.27 wt. %, product of Stepan). Sodium hydroxide (50% aq. solution) is added to pH 11 (about 24% of the total amount of 4 wt. % required). Citric acid (50% aq. solution, 6.2 wt. %) is added, followed by triethanolamine (3.45 wt. %). Bio-Soft® EC-690 (laureth-7, 90% actives, 27.8 wt. %, product of Stepan) is slowly added. The pH is adjusted to the 7.8 to 8.4 range, targeting 8.1 with the remaining aqueous sodium hydroxide solution. Sodium xylene sulfonate (40% actives, 4.30 wt. %) is added, followed by a preservative and the remaining deionized water (q.s. to 100 wt. %).

Preparation of an Ultra Laundry Detergent with $C_{16}$ MES and the Blend:

Deionized water (q.s. to 100 wt. %) is charged at 55-60° C. The concentrated blend prepared above (58.0 wt. %) is added while maintaining temperature between 50° C. and 60° C. The $C_{16}$ MES (87% actives, 10.34 wt. %) is slowly added and allowed to dissolve. The mixture is then allowed to cool to 35°

C. The experimental sample or cocamide DEA standard (5.0 wt. %) is then added slowly and mixing continues until the batch is homogeneous.

Cold-Water Cleaning Evaluation:

Laundry detergent (30 g, see Part A) is charged to the laundry machine, followed by soiled/stained fabric swatches that are attached to pillowcases. Wash temperature: 55° F. Rinse: 55° F. The swatches are detached from pillowcases, dried, and ironed. Swatches are scanned to measure the L*a*b*values, which are used to calculate a soil removal index (SRI) for each type of swatch. Finally, the ΔSRI is calculated, which equals the experimental sample SRI minus the SRI of a pre-determined standard laundry detergent formula (or control). When |ΔSRI|≥1, differences are perceivable to the naked eye. If the value of ΔSRI is greater than or equal to 1, the sample is superior. If ΔSRI is less than or equal to −1, the sample is inferior. If ΔSRI is greater than −1 and less than 1, the sample is considered equal to the standard.

The following standard soiled/stained fabric swatches are used: dust sebum on cotton (DSC); beef tallow (BT); kaolin clay and wool fat on polyester (WFK 30C), grass on cotton (GC); blueberry on cotton (BC); cocoa on cotton (EMPA 112); and blood/ink/milk on cotton (EMPA 116). At least three of each kind of swatch are used per wash. Swatches are stapled to pillowcases for laundering, and extra pillowcases are included to complete a six-pound load.

The same procedure is used to launder all of the pillowcases/swatches, with care taken to ensure that water temperature, wash time, manner of addition, etc. are held constant for the cold-water wash process. When the cycle is complete, swatches are removed from the pillowcases, dried at low heat on a rack, and pressed briefly with a dry iron.

A Hunter LabScan® XE spectrophotometer is used to determine the L*a*b* values to calculate the SRI for every type of swatch, and the stain removal index (SRI) is calculated as follows:

$$SRI = 100 - \sqrt{(L*_{clean} - L*_{washed})^2 + (a*_{clean} - a*_{washed})^2 + (b*_{clean} - b*_{washed})^2}$$

$$\Delta SRI = SRI_{sample} - SRI_{standard}$$

One test sample, C12-30, outperforms the control in the cold-water cleaning test (see Table 18).

TABLE 18

Performance in Cold-Water Cleaning: |ΔSRI| Values v. Cocamide DEA in a $C_{16}$ Methyl Ester Sulfonate (MES) Formulation ΔSRI values

| test sample | C12-30 |
|---|---|
| dust sebum on cotton (DSC) | −0.6 |
| beef tallow (BT) | 1.9 |
| pigment/lanolin (WFK 30C) | 0.0 |
| blueberry on cotton (BC) | 2.5 |
| cocoa on cotton (EMPA 112) | 0.3 |
| blood/ink/milk on cotton (EMPA 116) | −0.5 |
| grass on cotton (GC) | −0.5 |
| overall rating | superior |

Oil Field Products: Paraffin Dispersants
Asphaltenes Screening Test

During acid stimulation of an oil well, a blend of HCl, HF, and corrosion inhibitor is pumped down a well, allowed to stand, and then pumped out. During the transfer of the acid, small amounts of iron chloride are developed in the acid solution. Once the acid blend dissolves scales and deposits in the well bore, crude oil begins to flow and mixes with the acid solution in the well. The crude oil can solidify after acidizing, and asphaltenes have been associated with the problem. Thus, dispersants are commonly added to the acid to prevent the solidification.

Test Method:

A stock solution of iron-contaminated acid is made by adding 1% $FeCl_3$ to a 15% HCl acid solution. The sample dispersant to be tested (0.2 wt. %) is added to the acid stock solution (7.5 mL). A 15-mL vial is charged with the acid/dispersant mixture and crude oil (2.5 mL), and the vial is shaken vigorously for 30 s. The initial appearance is recorded. After standing at room temperature for 1 h, the appearance is again noted. The vial is placed in an oven (50° C.) for 24 h and its appearance is recorded. The vial is allowed to cool to room temperature and appearance is again noted. Finally, after 24 h at room temperature, appearance is again noted. A blank sample containing crude oil and acid solution but no dispersant is run. A control sample containing soy amidoamine trimethylammonium chloride as the dispersant is also run. Yet another sample is run containing a 1:1 mixture of test dispersant and soy amidoamine trimethylammonium chloride.

One sample, C18-66, provides superior performance as a paraffin dispersant.

Oilfield Corrosion Inhibition: Polarization Resistance Procedure

Polarization resistance is run in dilute NACE brine (3.5 wt. % NaCl; 0.111 wt. % $CaCl_2.2H_2O$; 0.068 wt. % $MgCl_2.6H_2O$) under sweet conditions ($CC_2$ sparged) at 50° C. The working electrode is cylindrical, made of C1018 steel, and rotates at 3000 rpm. The counter electrode is a platinum wire. The reference is a calomel electrode with an internal salt bridge. A baseline corrosion rate is established over at least a 3-h period. Once the baseline has been established, the corrosion inhibitor is injected and data is collected for the remainder of the test period. The desired inhibitor concentration is 0.00011-0.0010 meq/g active. Software details: initial delay is on at 1800 s with 0.05 mV/s stability; range: −0.02 to +0.02V; scan rate: 0.1 mV/s; sample period: 1 s; data collection: ~24 h. The final corrosion rate is an average of the last 5-6 h of data collection. Protection rate is calculated from:

$$\text{Protection Rate} = \frac{\left(\text{Initial Protection Rate [no inhibitor]} - \text{Final Protection Rate [with inhibitor]}\right) * 100}{\text{Initial Protection Rate [no inhibitor]}}$$

As shown in Table 19, two test samples show overall performance as corrosion inhibitors that equals that of the control.

TABLE 19

Performance in EOR Corrosion Inhibitors

| | Protection Rate (%) | | | |
|---|---|---|---|---|
| Sample | Low Dose | Mid Dose | High Dose | Overall Rating |
| Industry Std. A | 85 | 85 | 80 | |
| Control B | 66 | 83 | 76 | |
| Control C | 97 | 98 | 97 | |
| Control D | 90 | 98 | 85 | |
| C10-16 | 92 | 88 | 89 | good |
| C12-16 | 87 | 87 | 87 | good |

Performance as a Paint Additive
Paint Formulation:

Titanium dioxide slurry (Dupont Ti-Pure® R746) is charged to a container, followed by deionized water and propylene glycol, and the contents are mixed (500 rpm). Latex (49% solids) and preservative (Acticide® GA, product of Thor) are added. Thickener (Acrysol™ SCT-275, product of Dow, 0.3%) is slowly charged below the liquid surface by syringe. The pH is adjusted to 9.0 using ammonium hydroxide solution. The batch is mixed for 30 min. and then allowed to stand for at least 2 h. The batch is remixed gently, and a portion (240 g) is transferred to a 400-mL beaker. Solvent ($C_{18}$ amide) and derivative (1.76% active based on latex solids) are added and mixed at 650 rpm. Viscosity is adjusted to an initial KU of 90 with more thickener. The paint is covered and final KU is measured after 24 h. Its value falls within the range of 93-100 KU and varies from the original measurement by no more than 5 KU.

Example formulation: $TiO_2$ (solids basis): 24.35 wt. %; water: 46.39 wt. %; propylene glycol 2.59 wt. %; latex (solids basis) 22.76%; ammonium hydroxide: 0.04 wt. %; preservative: 0.10 wt. %; control additive (solvent): 1.14 wt. %; derivative (100% solids): 0.40 wt. %; thickener: 2.23 wt. %. PVC: 22.1%. VOC: <50 g/L. Final KU: 98.6.

Wet Scrub Resistance/ASTM 2486 Modified:

Wet scrub resistance based on a modified version of ASTM-2486-00, method B; modified to % weight loss, is performed for each paint formulation. Paints are applied to Leneta P-121-10N plastic panels using a 13-cm wide, 10-mil wet film applicator and dried under ambient conditions for five days prior to testing. The coated panels are then cut into strips (16.5 cm×5.7 cm, two per drawdown). The strips are weighed prior to testing. Two samples at a time are placed on a Gardner Company scrub tester with approximately a 2" gap between the samples and taped to secure panels to the machine. A spacer is placed over the samples to maintain the scrub brush pathway and further secure the samples. A scrub brush (8 cm×3 cm), preconditioned in room temperature water, is inserted into the holder. Scrub compound (10 g, supplied by Leneta Company as "ASTM-2486 scrub compound") is applied evenly to the brush. Water (5 g) is placed into the gap between the samples. Samples are tested to 1200 cycles. Additional scrub compound (10 g) and water (5 g) are reapplied every 300 cycles. The strips are then rinsed under tepid water and dried for 24 h. The strips are reweighed and the % coating removed is determined.

Wet Scrub Resistance/ASTM 2486 Shim Method

The procedure described above is used, except that a shim (ASTM accepted) is added prior to applying the coated panel strips. Cycles to fail is determined visually.

Gloss Determination—60°/20°—ASTM D523

Paints are applied to Leneta P-121-10N plastic panels using a wet film applicator (13 cm×10 mil) and dried under ambient conditions for 5 days prior to testing. Gloss is measured with an ASTM accepted glossmeter (Gardco).

Results:

One sample, C10-12, is superior as a paint additive (see Table 20).

TABLE 20

Performance as a Latex Paint Additive

| | 60° gloss | 20° gloss | % coating removed, scrub | shim scrub, cycles to fail | rating |
|---|---|---|---|---|---|
| Control 2 | 54.8 | 11.5 | 2.12 | 696 | — |
| C10-12 | 43.6 | 8.1 | 1.57 | 764 | superior |

Control 2 = $C_{12}$ dimethylamide

Performance as a Coalescing Solvent for an All-Acrylic Latex

An acrylic latex polymer (49% solids) is charged to a jar and mixed with a test sample at 5% level based on latex solids (0.6 g for a 100% active sample) for at least 16 h. A film is cast on a Rhopoint MFFT 90 instrument that is adjusted for a surface temperature gradient of 0° C. to 180° C. The minimum film forming temperature (MFFT) of the mixture is determined. Test samples are either evaluated as the only solvent or as 60:40 mixtures (control solvent to test sample). Control samples are also analyzed, including the latex alone and the latex plus control solvent. Results appear in Table 21.

TABLE 21

Performance as a Coalescing Solvent

| | latex, g | solvent, g | MFFT, ° C. | rating |
|---|---|---|---|---|
| latex only control | 25 | 0 | 13.3 | — |
| latex + solvent control | 25 | 0.6 | 3.2 | — |
| latex + 60:40 control/PMTG-15 | 25 | 0.6 | 3.8 | equal |
| latex only control | 25 | 0 | 13.3 | — |
| latex + solvent control | 25 | 0.6 | 3.8 | — |
| latex + 60:40 control/MTG-15 | 25 | 0.6 | 3.2 | equal |
| latex + MTG-15 | 25 | 0.6 | 5.4 | equal |
| latex only control | 25 | 0 | 14.2 | — |
| latex + solvent control | 25 | 0.62 | 4.3 | — |
| latex + Mix-59 | 25 | 0.62 | 5.4 | equal |

Control = $C_{18}$ dimethylamide

Performance as a Coalescing Solvent in a Latex Paint

Titanium dioxide slurry (Dupont Ti-Pure® R746) is charged to a container, followed by deionized water and propylene glycol, and the contents are mixed (500 rpm). Latex (49% solids) and preservative (Acticide® GA, product of Thor) are added. Thickener (Acrysol™ SCT-275, product of Dow, 0.3%) is slowly charged below the liquid surface by syringe. The pH is adjusted to 9.0 using ammonium hydroxide solution. The batch is mixed for 30 min. and then allowed to stand for at least 2 h. The batch is remixed gently, and a portion (240 g) is transferred to a 400-mL beaker. The derivatives are added as the solvent at a 2-5% level based on latex solids and mixed at 650 rpm. Viscosity is adjusted to 90KU with more thickener. The paint is covered and viscosity is measured after 24 h. Its value falls within the range of 93-100 KU and varies from the original measurement by no more than 5 KU.

Example formulation, 2% co-solvent with $C_{18}$ amide: $TiO_2$ (solids basis): 24.50 wt. %; water: 46.66 wt. %; propylene glycol 2.60 wt. %; latex (solids basis) 22.89%; ammonium hydroxide: 0.04 wt. %; preservative: 0.10 wt. %; control additive: 0.68%; derivative (100% solids): 0.46 wt. %; thickener: 2.07 wt. %. PVC: 22.1%. VOC: <50 g/L. Final KU: 103.7.

Example formulation, 5% solvent, derivative only: $TiO_2$ (solids basis): 24.43 wt. %; water: 46.54 wt. %; propylene glycol 2.60 wt. %; latex (solids basis) 22.84%; ammonium hydroxide: 0.05 wt. %; preservative: 0.10 wt. %; derivative: 1.14 wt. %; thickener: 2.30 wt. %. PVC: 22.1%. VOC: <50 g/L. Final KU: 97.7.

Results:

Four of the samples tested perform as well as the control solvent(s) in a latex paint. See Table 22.

TABLE 22

Performance as a Coalescing solvent in a paint

|  | 60° gloss | 20° gloss | % coating removed, scrub | rating |
|---|---|---|---|---|
| $C_{18}$ Amide | 54.8 | 11.5 | 2.12 | — |
| PMTG-15 (50%); $C_{18}$ Amide (50%) | 52.2 | 9.8 | 2.01 | equal |
| MTG-15 | 52.4 | 10 | 2.07 | equal |
| $C_{18}$ Amide | 64.9 | 18.1 | 2.47 | — |
| $C_{12}$ Amide | 67.6 | 21.3 | 2.41 | — |
| C12-25 | 66.6 | 19.7 | 2.54 | equal |
| $C_{18}$ Amide | 60.9 | 15.1 | 1.81 | — |
| Mix-59 | 61.7 | 15.9 | 1.87 | equal |

In another kind of test for evaluating coalescing solvents, thermogravimetric analysis (TGA) is used to determine the VOC content of a test sample compared with that of a control solvent. The instrument is set to measure weight loss over 60 min. at 110° C. Test sample C12-25 gives a value of 4.49% VOC, compared with 4.20% for the control sample, a $C_{12}$ dimethylamide. This indicates equal performance of C12-25 versus the control.

Antimicrobial Products: Biocide Actives

Biocidal efficiency is evaluated using the rapid screen assay, an ATP-based method that measures relative kill % of bacteria in a 5-min. period. The control used is first-generation ADBAC BTC 835 (benzyldimethylammonium chloride). Test organisms: *Pseudomonas aeruginosa* and *Staphylococcus aureas*.

Twenty-four hour old test organism cultures are prepared in Mueller Hinton broth and incubated. Samples are accurately weighed in deionized water or 400 ppm water to make a 1000 ppm solution taking into account the actives level of the sample. The 24-h culture is diluted to 10 vol. % to obtain a cell concentration of ~$10^7$ cfu/mL (colony forming units per mL). Reagents are prepared using the instructions provided in the BacTiter-Glo™ Microbial Cell Viability Assay kit (product of Promega) and calibrated at room temperature for 15 min. Each formulation type is dispensed (90 μL at 1000 ppm) into each row of a 96-well plate. Blank medium, i.e., Mueller Hinton broth (10 μL) is dispensed in three replicate wells (1-3) to determine baseline, while the organism to be tested (10 μL) is dispensed in nine experimental replicate wells (4-12). The timer is started, and the test plate (baseline and experimental) is shaken for 30 s. At the end of an appropriate contact time (e.g. 5 min or 10 min), an equal amount of BacTiter-Glo™ reagent mix is added to each reaction mixture, starting with the experimental samples and ending with the baseline samples. After shaking to ensure thorough mixing, the relative luminescence units (RLUs) of each well are measured and recorded. The % kill of $10^7$ cfu/mL after 5 min. contact time for each organism in DI or hard water is calculated from:

% Kill=[1−(Ave. RLU of Wells$_{Experimental}$−Ave. RLU of Wells$_{Baseline\ Controls}$)]/80000

As shown in Table 23, one tested composition performs as well as the control when tested as an antimicrobial active.

TABLE 23

Performance as Antimicrobial Active
% Kill at 5 min. contact time, $10^7$ cfu/mL, 1000 ppm

|  | *Pseudomonas aeruginosa* | | *Staphylococcus aureas* | | Overall |
|---|---|---|---|---|---|
|  | DI water | 400 ppm | DI water | 400 ppm | Rating |
| control | 25.5 | 18.3 | 50.2 | 46.6 |  |
| C12-13 | 27.1 | 13.7 | 48.3 | 33.1 | good | control = dimethylbenzylammonium chloride

The preceding examples are meant only as illustrations. The following claims define the invention.

We claim:

1. A method which comprises reacting a monounsaturated acid selected from the group consisting of 9-decenoic acid, 9-undecenoic acid, 9-dodecenoic acid, 9-tridecenoic acid, 9-tetradecenoic acid, 9-pentadecenoic acid, 9-hexadecenoic acid, 9-heptadecenoic acid, octadecene-1,18-dioic acid, and their ester derivatives, with ammonia or a primary or secondary amine, wherein the primary or secondary amine has one or two hydrogens attached to the amino group and the remaining groups are $C_1$-$C_{10}$ alkyl, $C_2$-$C_4$ hydroxyalkyl, or alkoxylated $C_2$-$C_4$ hydroxyalkyl, to produce a fatty amide, wherein the monounsaturated acid or its ester derivative has terminal $\Delta^9$ unsaturation or at least 1 mole % of trans-$\Delta^9$ unsaturation.

2. The method of claim 1 further comprising at least one step selected from the group consisting of reducing, quaternizing, sulfonating, alkoxylating, sulfating, and sulfitating the fatty amide to produce a fatty amide derivative.

3. The method of claim 1 comprising reacting two equivalents of the monounsaturated acid or its ester derivative with diethylenetriamine (DETA), (2-aminoethyl)ethanolamine (AEEA), or alkoxylated AEEA to produce an imidazoline amide or an imidazoline ester.

4. The method of claim 3 further comprising at least one step selected from the group consisting of reducing, quaternizing, sulfonating, alkoxylating, sulfating, and sulfitating the imidazoline amide ester to produce an imidazoline amide or ester derivative.

5. The method of claim 1 wherein the monounsaturated acid or its ester derivative has at least 50 mole % of trans-$\Delta^9$ unsaturation.

6. The method of claim 1 wherein the fatty amide has the formula:

$R^1CO—NR^2R^3$ where $R^1$ is  $R^4$—$C_9H_{16}$— or $R^5O_2C$—$C_{16}H_{30}$—; $R^4$ is hydrogen or $C_1$-$C_7$ alkyl; $R^5$ is substituted or unsubstituted alkyl, aryl, alkenyl, oxyalkylene, polyoxyalkylene, glyceryl ester, or a mono- or divalent cation; and each of $R^2$ and $R^3$ is independently H, $C_1$-$C_6$ alkyl, or —$CH_2CH_2OR^6$ where $R^6$ is H or $C_1$-$C_6$ alkyl.

7. The method of claim 1 wherein the primary or secondary amine is selected from the group consisting of ethanolamine, N-methylethanolamine and diethanolamine.

8. The method of claim 1 wherein the monounsaturated acid or its ester derivative comprises a mixture selected from the group consisting of: (a) a $C_{10}$ and a $C_{12}$ monounsaturated acid or ester derivative; (b) a $C_{10}$ and a $C_{14}$ monounsaturated acid or ester derivative; and (c) a $C_{10}$ and a $C_{16}$ monounsaturated acid or ester derivative.

9. The method of claim 1 further comprising using the fatty amide to formulate an anionic emulsifier for agricultural compositions, a nonionic emulsifier for agricultural compositions, a dispersant for agricultural compositions, a water-soluble herbicide composition, an agricultural solvent, an antimicrobial composition, an aqueous hard-surface cleaner, an industrial hard-surface cleaner, a laundry detergent formulation, a shampoo or hair conditioner, a personal cleanser or handsoap, a corrosion inhibitor or paraffin dispersant for use in oilfield applications, or a paint or coating additive composition.

10. The method of claim 2 further comprising using the fatty amide derivative to formulate an anionic emulsifier for agricultural compositions, a nonionic emulsifier for agricultural compositions, a dispersant for agricultural compositions, a water-soluble herbicide composition, an agricultural solvent, an antimicrobial composition, an aqueous hard-surface cleaner, an industrial hard-surface cleaner, a laundry detergent formulation, a shampoo or hair conditioner, a personal cleanser or handsoap, a corrosion inhibitor or paraffin dispersant for use in oilfield applications, or a paint or coating additive composition.

11. The method of claim 3 further comprising using the imidazoline amide or ester to formulate an anionic emulsifier for agricultural compositions, a nonionic emulsifier for agricultural compositions, a dispersant for agricultural compositions, a water-soluble herbicide composition, an agricultural solvent, an antimicrobial composition, an aqueous hard-surface cleaner, an industrial hard-surface cleaner, a laundry detergent formulation, a shampoo or hair conditioner, a personal cleanser or handsoap, a corrosion inhibitor or paraffin dispersant for use in oilfield applications, or a paint or coating additive composition.

12. The method of claim 4 further comprising using the imidazoline amide or ester derivative to formulate an anionic emulsifier for agricultural compositions, a nonionic emulsifier for agricultural compositions, a dispersant for agricultural compositions, a water-soluble herbicide composition, an agricultural solvent, an antimicrobial composition, an aqueous hard-surface cleaner, an industrial hard-surface cleaner, a laundry detergent formulation, a shampoo or hair conditioner, a personal cleanser or handsoap, a corrosion inhibitor or paraffin dispersant for use in oilfield applications, or a paint or coating additive composition.

* * * * *